US009447539B2

(12) United States Patent
Zhang et al.

(10) Patent No.: US 9,447,539 B2
(45) Date of Patent: Sep. 20, 2016

(54) METHODS FOR CONVERTING LIGNOCELLULOSIC MATERIAL TO USEFUL PRODUCTS

(71) Applicants: Syngenta Participations AG, Basel (CH); Queensland University of Technology, Brisbane, Queensland (AU)

(72) Inventors: Zhanying Zhang, Carina (AU); Ian Mark O'Hara, Grange (AU); William Orlando Sinclair Doherty, Calamvale (AU)

(73) Assignee: Syngenta Participations AG, Basel (CH)

( * ) Notice: Subject to any disclaimer, the term of this patent is extended or adjusted under 35 U.S.C. 154(b) by 118 days.

(21) Appl. No.: 14/100,340

(22) Filed: Dec. 9, 2013

(65) Prior Publication Data

US 2014/0093917 A1 Apr. 3, 2014

Related U.S. Application Data

(63) Continuation of application No. PCT/EP2012/060860, filed on Jun. 8, 2012.

(60) Provisional application No. 61/495,541, filed on Jun. 10, 2011, provisional application No. 61/570,438, filed on Dec. 14, 2011.

(51) Int. Cl.
| | |
|---|---|
| *D21B 1/02* | (2006.01) |
| *C13K 13/00* | (2006.01) |
| *C12P 19/14* | (2006.01) |
| *C12P 19/02* | (2006.01) |
| *C13K 1/02* | (2006.01) |
| *C08B 37/00* | (2006.01) |
| *C08H 7/00* | (2011.01) |
| *C08H 8/00* | (2010.01) |
| *C12P 7/10* | (2006.01) |

(52) U.S. Cl.
CPC ............ *D21B 1/021* (2013.01); *C08B 37/0006* (2013.01); *C08B 37/0057* (2013.01); *C08H 6/00* (2013.01); *C08H 8/00* (2013.01); *C12P 7/10* (2013.01); *C12P 19/02* (2013.01); *C12P 19/14* (2013.01); *C13K 1/02* (2013.01); *C13K 13/002* (2013.01); *C12P 2201/00* (2013.01); *C12P 2203/00* (2013.01); *Y02E 50/16* (2013.01)

(58) Field of Classification Search
CPC .... C13K 1/02; C13K 13/007; C13K 13/002; C12P 19/14; C12P 19/02; C12P 7/10; C12P 2201/00; C12P 2203/00; C08H 6/00; C08H 8/00; C08B 37/0057; C08B 37/0006; Y02E 50/16
See application file for complete search history.

(56) References Cited

U.S. PATENT DOCUMENTS

| 6,333,181 B1 | 12/2001 | Ingram et al. |
| 2008/0227162 A1* | 9/2008 | Varanasi .................. C12P 7/10 |
| | | 435/96 |
| 2009/0246841 A1 | 10/2009 | Jamieson et al. |
| 2009/0286293 A1 | 11/2009 | Kim et al. |
| 2011/0054059 A1 | 3/2011 | Li et al. |

FOREIGN PATENT DOCUMENTS

| CN | 101186560 | 5/2008 |
| CN | 101205287 | 6/2008 |
| CN | 101298744 A | 11/2008 |
| EP | 0 472 474 A1 | 2/1992 |
| JP | 2004-083482 | 3/2004 |
| WO | WO 2004/011518 A2 | 2/2004 |
| WO | WO 2004/081185 A2 | 9/2004 |
| WO | WO 2006/086861 A2 | 8/2006 |

OTHER PUBLICATIONS

Sun et al., Enhanced enzymatic hydrolysis of wheat straw by aqueous glycerol pretreatment, Bioresource Technology, 99, pp. 6156-6161, 2008.*
Martin et al., Effect of Glycerol Pretreatment on Component Recovery and Enzymatic Hydrolysis of Sugarcane Bagasse, Cellulose Chemistry and Technology, 45 (7-8), 487-494 (2011).*
Adeeb, Z., "Glycerol delignification of poplar wood chips in aqueous medium", Energy, Education, Science and Technology, 2004, 13: 81-88.
U.S. Appl. No. 14/100,486, filed Oct. 9, 2013, Zhang et al.
U.S. Appl. No. 14/100,510, filed Oct. 9, 2013, Zhang et al.
Alvira et al., "Pretreatment technologies for an efficient bioethanol production process based on enzymatic hydrolysis: A review", Bioresource Technology, 2010, 101(13): 4851-4861.
Araque et al., "Evaluation of organosolv pretreatment for the conversion of Pinus radiata D. Don to ethanol", Enzyme and Microbial Technology, 2008, 43(2): 214-219.
Behr et al., "Improved utilisation of renewable resources: New important derivatives of glycerol", Green Chemistry, 2008, 10(1): 13-30.
Borjesson et al., "Enhanced enzymatic conversion of softwood lignocellulose by poly(ethylene glycol) addition", Enzyme and Microbial Technology, 2007, 40(4): 754-762.

(Continued)

Primary Examiner — Taeyoon Kim
Assistant Examiner — Srikanth Patury
(74) Attorney, Agent, or Firm — Myers Bigel & Sibley, P.A.

(57) ABSTRACT

The present invention provides compositions and methods for the pretreatment of lignocellulosic material. The present invention further provides for pretreated lignocellulosic material that can be used to produce useful products, such as fermentable sugars.

16 Claims, 7 Drawing Sheets

(56) References Cited

OTHER PUBLICATIONS

Bouchard et al., "Mechanism of Depolymerization of Cellulose by Ethylene Glycol Solvolysis", *Holzforschung*, 1993, 47: 291-296.

Burchhardt et al., "Conversion of Xylan to Ethanol by Ethanologenic Strains of *Escherichia coli* and *Klebsiella oxytoca*", *Applied and Environmental Microbiology*, 1992, 58: 1128-1133.

Da Silva et al., "Glycerol: A promising and aboundant carbon source for industrial microbiology", *Biotechnology Advances*, 2009, 27: 30-39.

Demirbas, A., "Aqueous glycerol delignification of wood chips and ground wood", *Bioresource Technology*, 1998, 63(2): 179-185.

Demirbas et al., "Degradation of Poplar and Spruce Wood Chips Using Alkaline Glycerol", *Energy Sources, Part A*, 2005, 27: 1073-1084.

Demirbas, A., "Liquefaction of Biomass Using Glycerol", *Energy Sources, Part A*, 2008, 30: 1120-1126.

Demirbas, A., "Direct and Alkaline Glycerol Liquefaction of Hazelnut Shell", *Energy Sources, Part A*, 2010, 32: 689-696.

Dien et al., "Fermentation of hexose and pentose sugars using a novel ethanologenic *Escherichia coli* strain", *Enzyme and Microbial Technology*, 1998, 23: 366-371.

Guo et al., "Characterization of dilute acid pretreatment of silvergrass for ethanol production", *Bioresource Technology*, 2008, 99(14): 6046-6053.

Hassan et al., "Polyhydric Alcohol Liquefaction of Some Lignocellulosic Agricultural Residues", *Industrial Crops and Products*, 2008, 27: 33-38.

Hideno et al., "Development of environmentally-friendly pretreatment for ethanol production from lignocellulose", *Baiomasu Kagaku Kaigi Happyo Ronbunshu*, 2010, 5: 76-77.

Hormeyer et al., "Ethanol-Production by Clostridium-Thermocellum Grown on Hydrothermally and Organosolv-Pretreated Lignocellulosic Materials", *Applied Microbiology and Biotechnology*, 1988, 29(6): 528-535.

International Preliminary Report on Patentability and Written Opinion of the International Searching Authority Corresponding to International Application No. PCT/EP2012/060860; Date of Mailing: Dec. 27, 2013.

International Preliminary Report on Patentability and Written Opinion of the International Searching Authority Corresponding to International Application No. PCT/EP2012/060861; Date of Mailing: Dec. 10, 2013.

International Search Report and Written Opinion of the International Searching Authority Corresponding to International Application No. PCT/EP2012/060860; Date of Mailing: Sep. 27, 2012.

International Search Report and Written Opinion of the International Searching Authority Corresponding to International Application No. PCT/EP2012/060861; Date of Mailing: Aug. 13, 2012.

Jasiukaityte et al., "Cellulose liquefaction in acidified ethylene glycol", *Cellulose*, 2009, 16: 393-405.

Jimenez et al., "Ethyleneglycol pulp from tagasaste", *Bioresource Technology*, 2008, 99(7): 2170-2176.

Kucuk, M., "Delignification of Biomass Using Alkaline Glycerol", *Energy Sources, Part A*, 2005, 27(13): 1245-1255.

Lawford et al., "Fermentation of Biomass-Derived Glucuronic Acid by pet Expressing Recombinants of *E. coli* B", *Applied Biochemistry and Biotechnology*, 1997, 63-65: 221-241.

Lee et al., "Evaluation of Organosolv Processes for the Fractionation and Modification of Corn Stover for Bioconversion", *Biotechnology and Bioengineering*, 1987, 29: 572-581.

Lee et al., "Pretreatment of Waste Newspaper Using Ethylene Glycol for Bioethanol Production", *Biotechnology and Bioprocess Engineering*, 2010, 15(6): 1094-1101.

Li et al., "Improving enzymatic hydrolysis of wheat straw using ionic liquid 1-ethyl-3-methyl imidazolium diethyl phosphate pretreatment", *Bioresource Technology*, 2009, 100: 3570-3575.

Li et al., "Comparison of dilute acid and ionic liquid pretreatment of switchgrass: Biomass recalcitrance, delignification and enzymatic saccharification", *Bioresource Technology*, 2010, 101(13): 4900-4906.

Liu et al., "Corn stover pretreatment by inorganic salts and its effects on hemicellulose and cellulose degradation", *Bioresource Technology*, 2009, 100: 5865-5871.

Liu et al., "Microwave-assisted pretreatment of recalcitrant softwood in aqueous glycerol", *Bioresource Technology*, 2010, 101: 9355-9360.

Martin et al., "Effect of glycerol pretreatment on component recovery and enzymatic hydrolysis of sugarcane bagasse", *The Third Nordic Wood Biorefinery Conference*, (2011), Stockholm, Mar. 22-24.

Mosier et al., "Features of promising technologies for pretreatment of lignocellulosic biomass", *Bioresource Technology*, 2005, 96: 673-686.

Mun et al., "Evaluation of Organic Sulfonic Acids as Catalyst during Cellulose Liquefaction Using Ethylene Carbonate", *Journal of Industrial and Engineering Chemistry*, 2001, 7(6): 430-434.

Pan et al., "Strategies to enhance the enzymatic hydrolysis of pretreated softwood with high residual lignin content", *Applied Biochemistry and Biotechnology*, 2005, 121: 1069-1079.

Pan et al., "Pretreatment of lodgepole pine killed by mountain pine beetle using the ethanol organosolv process: Fractionation and process optimization", *Industrial and Engineering Chemistry Research*, 2007, 46(8): 2609-2617.

Park et al., "Cellulose crystallinity index: measurement techniques and their impact on interpreting cellulase performance", *Biotechnology for Biofuels*, 2010, 3.

Rezayati-Charani et al., "Influence of dimethyl formamide pulping of bagasse on pulp properties", *Bioresource Technology*, 2006, 97: 2435-2442.

Rezzoug et al., "Solvolysis of cellulose in acidified ethylene glycol: kinetics aspects", *Biomass for Energy, Environment, Agriculture and Industry, Proceedings of the European Biomass Conference*, 8th, Vienna, 1995.

Rezzoug et al., "Assessment of wood liquefaction in acidified ethylene glycol using experimental design methodology", *Energy Conversion and Management*, 2003, 44(5): 781-792.

Rinaldi et al., "An Integrated Catalytic Approach to Fermentable Sugars from Cellulose", *ChemSusChem*, 2010, 3: 1151-1153.

Rinaldi et al., "Which Controls the Depolymerization of Cellulose in Ionic Liquids: The Solid Acid Catalyst or Cellulose?", *ChemSusChem*, 2010, 3: 266-276.

Sanchez et al., "Trends in biotechnological production of fuel ethanol from different feedstocks", *Bioresource Technology*, 2008, 99(13): 5270-5295.

Shin et al., "Kinetic Study of Recycled Newspaper Liquefaction in Polyol Solvent", *Biotechnology and Bioprocess Engineering*, 2009, 14: 349-353.

Sluiter et al., "Determination of structural carbohydrates and lignin in biomass", *National Renewable Energy Laboratory*, 2008.

Sun et al., "Evaluation of enzymatic hydrolysis of wheat straw pretreated by atmospheric glycerol autocatalysis", *Journal of Chemical Technology and Biotechnology*, 2007, 82(11): 1039-1044.

Sun et al., "Comparison of atmospheric aqueous glycerol and steam explosion pretreatments of wheat straw for enhanced enzymatic hydrolysis", *Journal of Chemical Technology & Biotechnology*, 2008, 83(5): 707-714.

Sun et al., "Enhanced enzymatic hydrolysis of wheat straw by aqueous glycerol pretreatment", *Bioresource Technology*, 2008, 99: 6156-6161.

Sun et al., "Organosolv pretreatment by crude glycerol from oleochemicals industry for enzymatic hydrolysis of wheat straw", *Bioresource Technology*, 2008, 99(13): 5474-5479.

Tesser et al., "Kinetics of Glycerol Chlorination with Hydrochloric Acid: A New Route to alpha,gamma-dichlorohydrin", *Industrial & Engineering Chemistry Research*, 2007, 46(20): 6456-6465.

Vanasse et al., "Liquefaction of lignocellulosics in model solvents: creosote oil and ethylene glycol", *Canadian Journal of Chemical Engineering*, 1988, 66(1): 112-120.

Wang et al., "Study on thermochemical liquefaction of plant cellulose and the liquefaction products", *Shanxi Daxue Xuebao, Ziran Kexueban*, 2004, 27(1): 48-53.

(56) References Cited

OTHER PUBLICATIONS

Yamada et al., "Rapid liquefaction of lignocellulosic waste by using ethylene carbonate", *Bioresource Technology*, 1999, 70(1): 61-67.

Yamada et al., "Chemical analysis of the product in acid-catalyzed solvolysis of cellulose using polyethylene glycol and ethylene carbonate", *Journal of Wood Science*, 2007, 53(6): 487-493.

Zhang et al., "Mild liquefaction behavior of lignocellulosic material components", *Journal of Tsinghua University (Science and Technology)*, 2006, 46(12): 2011-2014.

Zhao et al., "Peracetic acid pretreatment of sugarcane bagasse for enzymatic hydrolysis: a continued work", *Journal of Chemical Technology and Biotechnology*, 2008, 83(6): 950-956.

Zhao et al., "Organosolv pretreatment of lignocellulosic biomass for enzymatic hydrolysis", *Applied Microbiology and Biotechnology*, 2009, 82: 815-827.

Hideno et al. "Development of environmentally-friendly pretreatment for ethanol production from lignocellulose" *Baiomasu Kagaku Kaigi Happyo Ronbunshu*, 5 (2010) (5 pages).

* cited by examiner (a)

(b)

(c)

(b)

US 9,447,539 B2

METHODS FOR CONVERTING LIGNOCELLULOSIC MATERIAL TO USEFUL PRODUCTS

RELATED APPLICATIONS

This application is a continuation under 35 U.S.C.§111(a) of PCT Application No. PCT/EP2012/060860, filed on Jun. 8, 2012, which claims the benefit, under 35 U.S.C. §119, of U.S. Provisional Application No. 61/570,438, filed on Dec. 14, 2011 and U.S. Provisional Application No. 61/495,541, filed on Jun. 10, 2011, the disclosures of each of which are incorporated herein by reference in their entirety.

FIELD OF THE INVENTION

The present invention concerns pretreatment solutions for lignocellulosic material and methods for pretreating lignocellulosic material that can be used to produce useful products, such as fermentable sugars.

BACKGROUND OF THE INVENTION

Lignocellulosic material can be used to produce biofuels (e.g., bioethanol) and biochemicals, and thus is an alternative to fossil fuels. For efficient biofuel production from lignocellulosic materials, the cellulose and/or hemicellulose components of lignocellulosic material need to be converted to monosaccharides (i.e., monosugars) that are capable of being fermented into ethanol or butanol. Prior work in this area has proposed processes for the production of fermentable sugars from lignocellulosic material that involve a chemical and/or physical pretreatment to disrupt the natural structure of the lignocellulosic material, followed by enzymatic hydrolysis of the cellulose and hemicellulose components into monosugars. The monosugars can then be fermented to produce biofuels including ethanol or butanol, and/or other fermentation products such as organic acids and/or other alcohols. However, these processes currently have not been commercialized due to the high cost, low efficiency, adverse reaction conditions, and other issues associated with the pretreatment process. In addition, these processes are not environmentally friendly and in order to achieve effective and efficient hydrolysis, a large addition of enzymes is required, which further increases costs.

The present invention addresses previous shortcomings in the art by providing pretreatment solutions for lignocellulosic material and methods for pretreating lignocellulosic material that can be used to produce fermentable sugars.

SUMMARY OF THE INVENTION

A first aspect of the present invention includes a pretreatment solution for lignocellulosic material comprising about 40% to about 99% by weight a polyol, about 0.1% to about 5% by weight an acid catalyst, and about 1% to about 60% by weight water.

A second aspect of the present invention is includes a method for producing a partially hydrolyzed lignocellulosic material, comprising pretreating a lignocellulosic material with a pretreatment solution comprising about 40% to about 99% by weight a polyol, about 0.1% to about 5% by weight an acid catalyst, and about 1% to about 60% by weight water, thereby producing a pretreated partially hydrolyzed lignocellulosic material.

A further aspect of the present invention includes a method for producing a fermentable sugar, comprising pretreating a lignocellulosic material with a pretreatment solution comprising about 40% to about 99% by weight a polyol, about 0.1% to about 5% by weight an acid catalyst, and about 1% to about 60% by weight water to produce a pretreated lignocellulosic material, and enzymatically hydrolyzing the pretreated lignocellulosic material, thereby producing a fermentable sugar.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
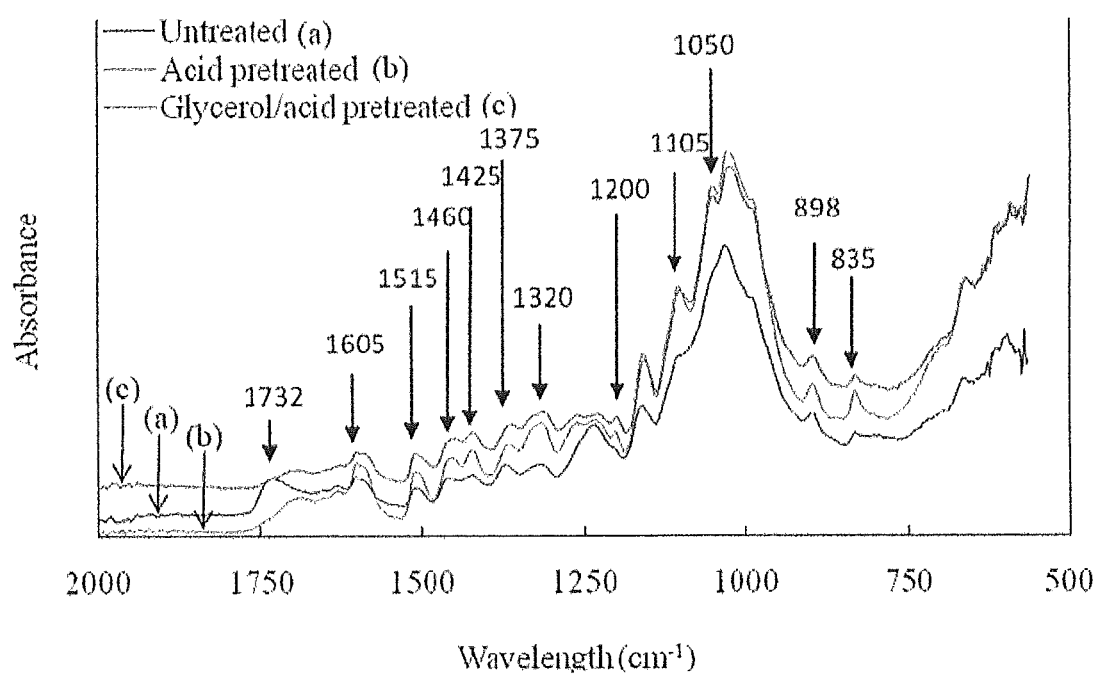
FIG. 1 shows FTIR spectra of (a) untreated bagasse, (b) bagasse pretreated with an acid solution, and (c) bagasse pretreated with a glycerol/acid/water solution.

The terminology used in the description of the invention herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

As used in the description of the invention and the appended claims, the singular forms "a", "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP§2111.03. Thus, the term "consisting essentially of" as used herein should not be interpreted as equivalent to "comprising."

The term "about," as used herein when referring to a measurable value such as an amount or concentration (e.g., the amount of polyol(s) in the pretreatment solution) and the like, is meant to encompass variations of 20%, 10%, 5%, 1%, 0.5%, or even 0.1% of the specified amount.

The present invention relates to pretreatment solutions for lignocellulosic material and methods for hydrolyzing lignocellulosic material that can subsequently be used to produce fermentable sugars.

"Lignocellulosic" or "lignocellulose", as used herein, refer to material comprising lignin and/or cellulose. Lignocellulosic material can also comprise hemicellulose, xylan, proteins, lipids, carbohydrates, such as starches and/or sugars, or any combination thereof. Lignocellulosic material can be derived from living or previously living plant material (e.g., lignocellulosic biomass). "Biomass," as used herein, refers to any lignocellulosic material and can be used as an energy source.

Lignocellulosic material (e.g., lignocellulosic biomass) can be derived from a single material or a combination of materials and/or can be non-modified and/or modified. Lignocellulosic material can be transgenic (i.e., genetically modified), "Transgenic", as used herein, refers to a plant into which a transgene has been delivered or introduced and the transgene can be expressed in the transgenic plant to produce a product, the presence of which can impart an effect and/or a phenotype in the plant. The term "transgene" as used herein, refers to any nucleic acid sequence used in the transformation of a plant. Thus, a transgene can be a coding sequence, a non-coding sequence, a cDNA, a gene or fragment or portion thereof, a genomic sequence, a regulatory element and the like. In some embodiments of the present invention, the lignocellulosic material is a transgenic plant or transgenic plant material that expresses or expressed exogenous enzymes.

Lignocellulose is generally found, for example, in the fibers, pulp, stems, leaves, hulls, canes, husks, and/or cobs of plants or fibers, leaves, branches, bark, and/or wood of trees and/or bushes. Exemplary lignocellulosic materials include, but are not limited to, agricultural biomass, e.g., farming and/or forestry material and/or residues, branches, bushes, canes, forests, grains, grasses, short rotation woody crops, herbaceous crops, and/or leaves; energy crops, e.g., corn, millet, and/or soybeans; energy crop residues; paper mill residues; sawmill residues; municipal paper waste; orchard prunings; chaparral; wood waste; logging waste; forest thinning; short-rotation woody crops; bagasse, such as sugar cane bagasse and/or sorghum bagasse, duckweed; wheat straw; oat straw; rice straw; barley straw; rye straw; flax straw; soy hulls; rice hulls; rice straw; tobacco; corn gluten feed; oat hulls; corn kernel; fiber from kernels; corn stover; corn stalks; corn cobs; corn husks; canola; miscanthus; energy cane; prairie grass; garnagrass; foxtail; sugar beet pulp; citrus fruit pulp; seed hulls; lawn clippings; cotton, seaweed; trees; shrubs; wheat; wheat straw; products and/or by-products from wet or dry milling of grains; yard waste; plant and/or tree waste products; herbaceous material and/or crops; forests; fruits; flowers; needles; logs; roots; saplings; shrubs; switch grasses; vegetables; fruit peels; vines; wheat midlings; oat hulls; hard and soft woods; or any combination thereof. In some embodiments, the lignocellulosic material has been processed by a processor selected from the group consisting of a dry grind ethanol production facility, a paper pulping facility, a tree harvesting operation, a sugar cane factory, or any combination thereof. In other embodiments of this invention, the lignocellulosic material is bagasse.

The methods of the present invention can comprise, consist essentially of, or consist of pretreating the lignocellulosic material (e.g., biomass) with a pretreatment solution of the present invention. "Pretreating", "pretreatment" and any grammatical variants thereof, as used herein refers to treating, contacting, soaking, suspending, immersing, saturating, dipping, wetting, rinsing, washing, submerging, and/ or any variation and/or combination thereof, the lignocellulosic material with a pretreatment solution of the present invention.

The pretreating step can be performed or carried out at a temperature from about 40° C. to about 150° C. or any range therein, such as, but not limited to, about 40° C. to about 90° C., about 50° C. to about 100° C., about 60° C. to about 90° C., about 80° C. to about 150° C., about 90° C. to about 130° C., or about 100° C. to about 130° C. In particular embodiments, the pretreatment step is carried out at a temperature of about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., 144° C., 145° C., 146° C., 147° C., 148° C., 149° C., 150° C., or any range therein. In, some embodiments of the present invention, the pretreatment step is carried out at a temperature of about 130° C. In other embodiments of the present invention, the pretreatment step is carried out at a temperature from about 40° C. to about 90° C.

The pretreating step can be performed or carried out for a period of time from about 1 minute to about 120 minutes or any range therein, such as, but not limited to, about 5 minutes to about 100 minutes, or about 15 minutes to about 60 minutes. In particular embodiments, the pretreatment step is carried out for a period of time of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, or any range therein. In certain embodiments of the present invention, the pretreatment step is carried out for a period of time of about 60 minutes.

Lignocellulosic biomass loading (i.e. the lignocellulosic material to pretreatment solution ratio) can be from about 0.1% to about 60% or any range therein, such as, but not limited to, about 5% to about 40%, or about 5% to about 20% by weight of the pretreatment solution. In particular embodiments, the lignocellulosic biomass loading is about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or any range therein, by weight of the pretreatment solution. In certain embodiments of the present invention, the lignocellulosic biomass loading is about 10% by weight of the pretreatment solution.

In representative embodiments of the present invention, a pretreatment solution of the present invention can comprise, consist essentially of, or consist of a polyol, an acid catalyst, water, or any combination thereof. Exemplary polyols include, but are not limited to, 1,2-propanediol, 1,3-propanediol, glycerol, 2,3-butanediol, 1,3-butanediol, 2-methyl-1,3-propanediol, 1,2-pentanediol, 1,3-pentanediol, 1,4-pentanediol, 1,5-pentanedial, 2,2-dimethyl-1,3-propanediol, 2-methyl-1,4-butanediol, 2-methyl-1,3-butanediol, 1,1,1-trimethylolethane, 3-methyl-1,5-pentanediol, 1,1,1-trimethylolpropane, 1,7-heptanediol, 2-ethyl-1,6-hexanediol, 1,9-nonanediol, 1,11-undecanediol, diethylene glycol, triethylene glycol, oligoethylene glycol, 2,2'-thiodiglycol, diglycols or polyglycols prepared from 1,2-propylene oxide, propylene glycol, ethylene glycol, sorbitol, dibutylene glycol, tributylene glycol, tetrabutylene glycol, dihexylene ether glycol, trihexylene ether glycol, tetrahexylene ether glycol, 1,4-cyclohexanediol, 1,3-cyclohexanediol, or any combination thereof. In particular embodiments of the present invention, the polyol is glycerol and/or ethylene glycol.

A polyol can be present in pure (e.g., refined) or impure (e.g., crude or purified crude) form. In certain embodiments of the present invention, a polyol has a purity of about 70% to about 99.9% or any range therein, such as, but not limited to, about 80% to about 99.9%, or about 80% to about 97%. In particular embodiments of the present invention, the purity of a polyol is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range therein. Purity forms or grades (e.g., refined, crude, or purified crude) of a polyol can be, but are not limited to, purity grades produced as by-products from biodiesel production processes. In particular embodiments of the present invention, a polyol is in pure form (e.g., having a purity of 99% or more) and in other embodiments a polyol is in crude form (e.g., having a purity of from about 70% to about 98%).

In some embodiments of the present invention, one or more polyols can be present in the pretreatment solutions of the present invention. For example, 1, 2, 3, 4, 5, or more polyols can be present in the pretreatment solutions of the present invention. A polyol can be present in the pretreatment solution in an amount from about 1% to about 99% by weight of the pretreatment solution or any range therein, such as, but not limited to, about 1% to about 80%, about 10% to about 50%, about 15% to about 35%, about 20% to about 99%, about 40% to about 99%, or about 80% to about 97% by weight of the pretreatment solution. In particular embodiments of the present invention, a polyol is present in the pretreatment solution in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or any range therein, by weight of the pretreatment solution. In certain embodiments of the present invention, a polyol is present in an amount from about 80% to about 99% by weight of the pretreatment solution.

In some embodiments of the present invention, one or more acid catalysts can be present in the pretreatment solutions of the present invention. For example, 1, 2, 3, 4, 5, or more acid catalyst(s) can be present in the pretreatment solutions of the present invention. An acid catalyst can be present in the pretreatment solution in an amount from about 0.1% to about 10% or any range therein such as, but not limited to, about 0.1% to about 5%, about 0.1% to about 1.5%, or about 1% to about 3% by weight of the pretreatment solution. In particular embodiments of the present invention, an acid catalyst is present in the pretreatment solution in an amount of about 0.1%, 0.2%, 0.3%, 0.4%, 0.5%, 0.6%, 0.7%, 0.8%, 0.9%, 1%, 1.2%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, or any range therein, by weight of the pretreatment solution. In certain embodiments of the present invention, an acid catalyst is present in an amount of about 0.5% to about 2% by weight of the pretreatment solution.

"Acid catalyst", as used herein refers to various water-soluble compounds with a pH of less than 7 that can be reacted with a base to form a salt. Exemplary acid catalysts can be monoprotic or polyprotic and can comprise one, two, three, or more acid functional groups. Exemplary acid catalysts include, but are not limited to, mineral acids, Lewis acids, acidic metal salts, organic acids, solid acids, inorganic acids, or any combination thereof. Specific acid catalysts include, but are not limited to hydrochloric acid, sulfuric acid, phosphoric acid, hydrofluoric acid, hydrobromic acid, hydroiodic acid, nitric acid, formic acid, acetic acid, methanesulfonic acid, toluenesulfonic acid, boron trifluoride diethyletherate, scandium (III) trifluoromethanesulfonate, titanium (IV) isopropoxide, tin (IV) chloride, zinc (II) bromide, iron (II) chloride, iron (III) chloride, zinc (II) chloride, copper (I) chloride, copper (I) bromide, copper (II) chloride, copper (II) bromide, aluminum chloride, chromium (II) chloride, chromium (III) chloride, vanadium (III) chloride, molybdenum (III) chloride, palladium (II) chloride, platinum (II) chloride, platinum (IV) chloride, ruthenium (III) chloride, rhodium (III) chloride, zeolites, activated zeolites, or any combination thereof. In certain embodiments, the acid catalyst is hydrochloric acid.

Water can optionally be present in the pretreatment solution in an amount from about 0% to about 80% or any range therein, such as, but not limited to, about 1% to about 60% or about 1% to about 20% by weight of the pretreatment solution. In particular embodiments of the present invention, water is present in the pretreatment solution in an amount of about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, or any range therein, by weight of the pretreatment solution. In certain embodiments, water is present in an amount from about 5% to about 20% by weight of the pretreatment solution.

In some embodiments of the present invention, a pretreatment solution comprises, consists essentially of, or consists of about 10% to about 99% by weight a polyol, about 0.1% to about 5% by weight an acid catalyst, and about 0% to about 60% by weight water. In other embodiments of the present invention, a pretreatment solution comprises, consists essentially of or consists of about 40% to about 99% by weight a polyol, about 0.1% to about 5% by weight an acid catalyst, and about 1% to about 60% by weight water.

In certain embodiments of the present invention, a pretreatment solution comprises, consists essentially of, or consists of about 85% to about 93% by weight a polyol, about 0.5% to about 2% by weight an acid catalyst, and about 5% to about 15% by weight water. In particular embodiments of the present invention, a pretreatment solution comprises, consists essentially of, or consists of about 88.8% by weight a polyol, about 1.2% by weight an acid catalyst, and about 10% by weight water. In some embodiments of the present invention, a polyol comprises glycerol.

The pretreatment step can result in the hydrolysis and/or break down of the lignocellulosic material. "Hydrolysis", as used herein, refers to the cleavage or breakage of the chemical bonds that hold the lignocellulosic material together. For instance, hydrolysis can include, but is not limited to, the breaking or cleaving of glycosidic bonds that link saccharides (i.e., sugars) together, and is also known as saccharification. Lignocellulosic material, in some embodiments, can comprise cellulose and/or hemicellulose. Cellulose is a glucan, which is a polysaccharide. Polysaccharides are polymeric compounds that are made up of repeating units of saccharides monosaccharides or disaccharaides) that are linked together by glycosidic bonds. The repeating units of saccharides can be the same (i.e., homogenous) to result in a homopolysaccharide or can be different (i.e., heterogeneous) to result in a heteropolysaccharide. Cellulose can undergo hydrolysis to form cellodextrins (i.e., shorter polysaccharide units compared to the polysaccharide units before the hydrolysis reaction) and/or glucose (i.e. a monosaccharide). Hemicellulose is a heteropolysaccharide and can include polysaccharides, including, but not limited to, xylan, glucuronoxylan, arabinoxylan, glucomannan and xyloglucan. Hemicellulose can undergo hydrolysis to form shorter polysaccharide units, and/or monosaccharides, including, but not limited to, pentose sugars, xylose, mannose, glucose, galactose, rhamnose, arabinose, or any combination thereof.

In some embodiments of the present invention, the pretreatment step partially hydrolyzes the lignocellulosic material. "Partial hydrolysis" or "partially hydrolyzes" and any grammatical variants thereof, as used herein, refer to the hydrolysis reaction cleaving or breaking less than 100% of the chemical bonds that hold the lignocellulosic material together. In other embodiments of the present invention, the hydrolysis reaction cleaves or breaks less than 100% of the glycosidic bonds of the cellulose and/or hemicellulose present in the lignocellulosic material. In some embodiments, the partial hydrolysis reaction can convert less than about 20%, 15%, 10%, or 5% of the cellulose into glucose. In further embodiments of this invention, the partial hydrolysis reaction can convert less than about 20%, 15%, 10%, or 5% of the hemicellulose into monosaccharides. Exemplary monosaccharides include but are not limited to, xylose, glucose, mannose, galactose, rhamnose, and arabinose. In some embodiments, the partial hydrolysis reaction can result in the recovery of greater than about 80%, 85%, 90%, or 95% of the glucan present in the pretreated lignocellulosic material compared to the amount of glucan present in the lignocellulosic material before pretreatment. In some embodiments of the present invention, the partial hydrolysis reaction can result in the recovery of less than about 40%, 35%, 30%, 25%, 20%, 15%, 10%, or 5% of the xylan in the pretreated lignocellulosic material compared to the amount of xylan present in the lignocellulosic material before pretreatment.

In particular embodiments of the present invention, the production of undesirable products from lignocellulosic material as a result of the pretreatment step is reduced compared to other processes for the treatment of lignocellulosic material. As used herein, the terms "reduce," "reduces," "reduced," "reduction" and similar terms refer to a decrease of at least about 5%, 10%, 25%, 35%, 50%, 75%, 80%, 85%, 90%, 95%, 97% or more. Exemplary undesirable products include furfural, acetic acid, 5-hydroxymethylfurfural (HMF), formic acid, and glycerol chlorination products, including, but not limited to, 3-monochloropropane-1,2-diol (3-MCPD), 2-monochloropropane-1,3-diol (2-MCPD), 1,3-dichloropropane-2-ol (1,3-DCP) and 1,2-dichloropropane-3-ol (1,2-DCP). In some embodiments, the undesirable product is at a concentration in the pretreatment solution, filtrate and/or hydrolysate of less than about 20 g/kg, 15 g/kg, 10 g/kg, 5 g/kg, 1 g/kg, 0.5 g/kg, or 0.25 g/kg and is thus reduced compared to other processes for treating lignocellulosic material. In other embodiments, the undesirable product is at a concentration in the pretreatment solution, filtrate and/or hydrolysate of less than about 0.25, 0.5, 1, 2, 3, 4, 5, 6, 7, 8, 9, 10, 11, 12, 13, 14, 15, 16, 17, 18, 19, 20 g/kg, or any range therein, and is thus reduced compared to other processes for treating lignocellulosic material.

In some embodiments of the present invention, the pretreatment step can break down and/or remove the lignin present in the lignocellulosic material. Lignin, in some embodiments, can be removed from the lignocellulosic material by hydrolysis of the chemical bonds that hold the lignocellulosic material together. Accordingly, in some embodiments of the present invention, the pretreatment step can result in the removal of about 80% or less (e.g., about 80%, 75%, 70%, 65%, 60%, 55%, 50%, 45%, 40%, 35%, 30%, 25%, 20%, etc.) or any range therein of the lignin in the pretreated lignocellulosic material compared to the amount of lignin present in the lignocellulosic material prior to the pretreating step. In some embodiments, the pretreatment step can result in the recovery of about 20% or more (e.g., about 20%, 25%, 30%, 35%, 40%, 45%, 50%, 55%, 60%, 65%, 70%, 75%, 80%, etc.) or any range therein of the lignin in the pretreated lignocellulosic material compared to the amount of lignin present in the lignocellulosic material prior to the pretreating step.

In other embodiments of the present invention, the pretreatment step can affect the structure of the lignocellulosic material. For instance, the pretreatment step can result in the dissociation of fibers in the lignocellulosic material, increase the porosity of the lignocellulosic material, increase the specific surface area of the lignocellulosic material, or any combination thereof. In some embodiments, the pretreatment step reduces the crystallinity of the cellulose structure by, for example, changing a portion of the cellulose from a crystalline state to an amorphous state.

The pretreatment step, in some embodiments of this invention, can make the pretreated lignocellulosic material more susceptible to enzymatic digestion compared to lignocellulosic material not subjected to a pretreatment step described herein. Thus, in some embodiments of the present invention, enzymatic digestion of the pretreated lignocellulosic material can be increased by two, three, four, five, six, seven, eight or more times compared to the enzymatic digestion of lignocellulosic material not pretreated with the pretreatment solution as described herein.

In further embodiments of the present invention, after treatment of the lignocellulosic material with the pretreatment solution as described herein, the lignocellulosic material can be separated from the pretreatment solution by any means known to those skilled in the art. A method of separating the lignocellulosic material from the pretreatment solution can include, but is not limited to, vacuum filtration, membrane filtration, sieve filtration, partial or coarse separation, or any combination thereof. The separating step can produce a liquid portion (i.e., filtrate or hydrolysate) and a solid residue portion (i.e., the pretreated lignocellulosic material). In some embodiments of the present invention, water is added to the pretreated lignocellulosic material before and/or after separation. Thus, in some embodiments, the pretreated lignocellulosic material can optionally include the pretreatment solution and/or by-products from the pretreatment process, such as, but not limited to, polyol(s), glycerol residue, acid(s), and products produced from the pretreatment process.

Optionally, after pretreatment of the lignocellulosic material with the pretreatment solution, as described herein, the pretreated lignocellulosic material can be washed with a post-pretreatment wash solution. A post-pretreatment wash solution can comprise a basic solution and/or an organic solvent. A basic solution can have a pH of about pH 8 or greater (e.g., about pH 8, 9, 10, 11, 12, 13, or 14). In particular embodiments, the pH of a basic solution is about pH 10 or greater or about pH 12 or greater. A basic solution can comprise alkaline chemicals, such as, but not limited to, sodium hydroxide, potassium hydroxide, ammonium hydroxide, and basic salts such as, but not limited to, sodium carbonate and potassium carbonate. The concentration of the alkaline chemical in the basic solution can be from about 0.0002% to about 0.12% by weight of the basic solution or any range therein, such as, but not limited to from about 0.002 to about 10%, about 0.02 to about 5%, or about 0.01 to about 0.5% by weight of the basic solution. In particular embodiments, the concentration of the alkaline chemical in the basic solution is about 0.2% by weight of the basic solution. In some embodiments of the present invention, a post-pretreatment wash solution comprises an organic solvent. Exemplary organic solvents for a post-pretreatment wash solution include, but are not limited, an alcohol, such as methanol and/or ethanol, acetone, and/or 1,4-dioxane.

A post-pretreatment wash can be carried out at a temperature from about 0° C. to about 100° C. or any range therein, such as, but not limited to, from about 5° C. to about 80° C., about 5° C. to about 40° C., or about 15° C. to about 35° C. In particular embodiments, the post-pretreatment wash is carried out at about room temperature (i.e., about 25° C.).

In some embodiments of the present invention, a post-pretreatment wash with a post-pretreatment wash solution can be carried out before and/or after the pretreated lignocellulosic material is optionally washed with water. According to some embodiments of the present invention, the pretreated lignocellulosic material can be washed with water and/or a post-pretreatment wash solution one or more times, such as 2, 3, 4, or more times. In certain embodiments of the present invention, the pretreated lignocellulosic material can be washed with a basic solution after pretreatment. In other embodiments of the present invention, the pretreated lignocellulosic material can be washed with water one or more times after pretreatment, then the pretreated lignocellulosic material is washed with a basic solution one or more times, followed by optionally washing the pretreated lignocellulosic material with water one or more times. In some embodiments of the present invention, the pretreated lignocellulosic material can be washed with an organic solvent one or more times, then washed with water one or more times. In further embodiments of the present invention, after the one or more water and/or post-pretreatment wash solution washes, the pretreated lignocellulosic material can be separated from the water and/or post-pretreatment wash solution via methods such as, but not limited to, vacuum filtration, membrane filtration, sieve filtration, partial or coarse separation, or any combination thereof.

In certain embodiments of the present invention, a post-pretreatment wash with a post-pretreatment wash solution removes lignin present in the pretreated lignocellulosic material. In particular embodiments, a post-pretreatment wash with a post-pretreatment wash solution removes residual lignin present in the pretreated lignocellulosic material. The residual lignin can, in some embodiments, be present in the pretreated lignocellulosic material as a result of lignin condensing on the pretreated lignocellulosic material during and/or after pretreatment with a pretreatment solution of the present invention. In some embodiments of the present invention, the lignin present in the pretreated lignocellulosic material can be dissolved and/or removed by washing the pretreated lignocellulosic material with a post-pretreatment wash solution.

In some embodiments of the present invention, after pretreatment, the wash with a post-pretreatment wash solution can result in the removal of about 25% or more of lignin as compared to the lignin present in untreated lignocellulosic material (i.e., lignocellulosic material not treated with a pretreatment solution of the present invention and/or not treated with a post-pretreatment wash solution of the present invention). In certain embodiments of the present invention, after pretreatment, a wash with a post-pretreatment wash solution can result in the removal of about 25%, 30%, 35%, 40%, 45%, 50%, 55%, or more, or any range therein, of lignin compared to the lignin present in untreated lignocellulosic material. In particular embodiments of the present invention, after pretreatment, a wash with a post-pretreatment wash solution can result in the removal of about 25% to about 50%, or any range therein, of lignin as compared to the lignin present in untreated lignocellulosic material. Thus, in some embodiments, after a pretreatment and/or a post-pretreatment wash as described herein, the amount of lignin removed from the lignocellulosic material (i.e., the sum of the lignin removed from a pretreatment with a pretreatment solution of the present invention and a post-pretreatment wash with a post-pretreatment wash solution of the present invention) is about 60% or more, such as about 60%, 65%, 70%, 75%, 80%, 85%, 90%, 95%, or more compared to the lignin present in untreated lignocellulosic material. In certain embodiments, pretreatment with a pretreatment solution of the present invention and post-pretreatment with a post-pretreatment wash solution of the present invention removes about 65% of the lignin present in the lignocellulosic material prior to pretreatment and post-pretreatment. In certain embodiments of the present invention, the post-pretreatment wash solution is a basic solution Optionally, a post-pretreatment wash solution can be collected after washing the pretreated lignocellulosic material. In some embodiments of the present invention, the collected post-pretreatment wash solution is a basic solution that can be used to recover lignin by adjusting the pH of the collected basic solution to an acidic pH (i.e., a pH of less than about 7) with an acid salt or acid, such as, but not limited to, hydrochloric acid, sulfuric acid, nitric acid, and phosphoric acid. In certain embodiments of the present invention, the pH of the collected basic solution is adjusted to a pH of about 1 to about 7 or any range therein, such as, but not limited to, about 1.5 to about 6.5 or about 2 to about 5. In some embodiments of the present invention, the temperature at which lignin is recovered can be from about 0° C. to about 90° C. or any range therein, such as, but not limited to, about 5° C. to about 70° or about 5° C. to about 40° C. The lignin can be recovered by precipitating the lignin from the collected basic solution and can be collected by filtration, such as, but not limited to, vacuum filtration, membrane filtration, sieve filtration, partial or coarse separation, or any combination thereof. The recovered lignin can be used for the production of a valuable product, such as, but not limited to, a combustion energy product, a phenol substitute in phenolic resins, a polymer additive, a construction material, or any combination thereof.

Without being bound to a particular theory, it is believed that the presence of lignin in the pretreated lignocellulosic material negatively affects the enzymatic hydrolysis of cellulose due to non-productive adsorption of the enzymes, such as cellulase, by lignin. Non-productive adsorption of the enzymes by lignin is believed to reduce the actual amount of the enzyme available for enzymatic hydrolysis. Thus, it is believed that by further removal of lignin present in the pretreated lignocellulosic material can improve the rate of enzymatic hydrolysis and reduce the amount of enzyme utilized in the enzymatic hydrolysis. The filtrate or hydrolysate can be collected after and/or during separation for use in pretreating additional lignocellulosic material (i.e., recycling of the filtrate/hydrolysate). The filtrate or hydrolysate can be collected and reused two, three, four, or more times. Additional components can optionally be added to the recycled solution, including but not limited to, additional water, acid catalyst(s), polyol(s), or any combination thereof. In some embodiments of the present invention, water is added to the recycled solution.

In some embodiments of the present invention, a pretreated lignocellulosic material can be subject to further processing conditions, such as, but not limited to, steam explosion.

In other embodiments of the present invention, the lignocellulosic material is treated with an aqueous acid solution prior to treatment with the pretreatment solution of the present invention (i.e., pre-pretreatment). An aqueous acid solution can comprise, consist essentially of, or consist of mineral acids, Lewis acids, acidic metal salts, organic acids, solid acids, inorganic acids, or any combination thereof. One or more acids (e.g., 1, 2, 3, 4, 5, or more acids) can be present in the aqueous acid solution, and the acid(s) can be monoprotic or polyprotic and can comprise one, two, three, or more acid functional groups. Exemplary acids include, but are not limited to hydrochloric acid, sulfuric acid, phosphoric acid, hydrofluoric acid, hydrobromic acid, hydroiodic acid, nitric acid, formic acid, acetic acid, methanesulfonic acid, toluenesulfonic acid, boron trifluoride diethyletherate, scandium (III) trifluoromethanesulfonate, titanium (IV) isopropoxide, tin (IV) chloride, zinc (II) bromide, iron (II) chloride, iron (III) chloride, zinc (II) chloride, copper (I) chloride, copper (I) bromide, copper (II) chloride, copper (II) bromide, aluminum chloride, chromium (II) chloride, chromium (III) chloride, vanadium (III) chloride, molybdenum (III) chloride, palladium (II) chloride, platinum (II) chloride, platinum (IV) chloride, ruthenium (III) chloride, rhodium (III) chloride, zeolites, activated zeolites, or any combination thereof. In certain embodiments, the acid in the aqueous acid solution is hydrochloric acid.

In some embodiments of this invention, the acid(s) can be present in the aqueous acid solution in an amount from about 0.1% to about 5% or any range therein, such as, but not limited to, about 0.1% to about 2.5% by weight of the acid solution. Thus, in some embodiments of the present invention, the acids) can be present in the acid solution in an amount of about 0.1%, 0.25%, 0.5%, 0.75%, 1%, 1.2%, 1.5%, 1.75%, 2%, 2.25%, 2.5%, 2.75%, 3%, 3.25%, 3.5%, 3.75%, 4%, 4.25%, 4.5%, 4.75%, 5%, or any range therein.

Another aspect of the present invention, provides a method of contacting the pretreated lignocellulosic material with at least one enzyme or an enzyme composition comprising at least one enzyme. In some embodiments, the pretreated lignocellulosic material can include the pretreatment solution and/or by-products from the pretreatment process, such as, but not limited to, polyol(s), glycerol residue, acid(s), and products produced from the pretreatment process. In certain embodiments, a method of the present invention can increase the enzymatic digestibility of a pretreated lignocellulosic material compared to the enzymatic digestibility of untreated lignocellulosic material (i.e., lignocellulosic material not treated as described herein). In some embodiments, a method of the present invention can increase enzymatic digestibility of a pretreated lignocellulosic material by at least about 2 times or 3 times compared to the enzymatic digestibility of untreated lignocellulosic material.

An enzyme can be microbially produced and/or plant produced, and can include, but is not limited to, a cellulase, a hemicellulase, a xylanase, a ligninase, a pectinase, a protease, an amylase, a catalase, a cutinase, a glucanase, a glucoamylase, a glucose isomerase, a lipase, a laccase, a phytase, a pullulanase, a xylose isomerase, or any combination thereof. The enzyme compositions can be prepared as a liquid, slurry, solid or gel. In one aspect of the present invention, the enzyme is/was expressed by the lignocellulosic plant material and retains its functional activity after pretreatment of the lignocellulosic material with the pretreatment solution. Accordingly, in some embodiments of the present invention, no additional enzyme(s) are contacted/added to the pretreated lignocellulosic material for enzymatic hydrolysis.

In particular embodiments of the present invention, the enzyme is a cellulase and/or xylanase. "Cellulase" or "cellulases", as used herein, refer to an enzyme capable of hydrolyzing cellulose to glucose. Non-limiting examples of cellulases include mannan endo-1,4-β-mannosidase, 1,3-β-D-glucan glucanohydrolase, 1,3-β-glucan glucohydrolase, 1,3-1,4-β-D-glucan glucanohydrolase and 1,6-β-D-glucan glucanohydrolase.

"Xylanase" or "xylanases", as used herein, refer to an enzyme capable of at least hydrolyzing xylan to xylobiose and xylotriose. Exemplary xylanases can be from a *Dictyoglomus* sp. including, but not limited to, *Dictyoglomus thermophilum* Rt46B.1. See, e.g., Gibbs et al. (1995) *Appl. Environ. Microbial.* 61:4403-4408.

In some embodiments of the present invention, an enzyme can be a high-temperature thermostable) and/or low-pH (i.e., acidophilic) tolerant enzyme. By "thermostable" or "thermotolerant" is meant that the enzyme retains at least about 70% activity at about 60° C. for 30 minutes, at least about 65% activity at about 70° C. for 30 minutes, or at least about 60% activity at about 80° C. for 30 minutes. "Acidophilic", as used herein, means that the enzyme retains about 60% to about 90% of its activity at pH 6, retains at least about 65% activity at pH 5.0, or retains at least about 60% activity at pH 4.0.

In some embodiments of the present invention, an enzyme can be a dual activity enzyme. A "dual activity enzyme", as used herein, refers to an enzyme having both xylanase and cellulase activity. The dual activity enzyme can be thermotolerant and/or acidophilic.

Additional nonlimiting examples of enzymes include α-L-arabinofuranosidase, α-glucuronidase, acetyl mannan esterase, acetyl xylan esterase, α-galactosidase, β-glucosidase, exoxylanase, β-1,4-xylosidase, endo-1,4-β-xylanase, endo-galactanase, endo-β-1,4-mannanase, 1,4-β-D-glucan cellobiohydrolase, endo-1,4-β-D-glucanase, β-glucosidase, endo-α-1,5-arabinanase, exo-β-1,4-mannosidase, cellobiohydrolases, endoglucanase, exo-β-1,4-xylosidase, feruloyl esterase, ferulic acid esterase, p-cumaric acid esterase, glucuronoxylan xylanohydrolase, xyloglucan endotransglycosylase, diarylpropane peroxidase, glucose oxidase, glyoxal oxidase, lignin peroxidase (LiP), manganese peroxidase, methanol oxidase, methanol oxidoreductase, phenol oxidase (laccase), phenol peroxidase, veratryl alcohol oxidase, pectolyase, pectozyme, polygalacturonase, asclepain, bromelain, caricain, chymopapain, collagenase, glycyl endopeptidase, pepsin, pronase, subtilisin, thermolysin or any combination thereof.

An enzyme can be provided as a partially or fully purified full-length enzyme, or active variants or fragments thereof, or can be provided as an enzyme-producing microorganism. Moreover, any of these enzymes can be provided in an amount effective to hydrolyze their substrate (e.g., the pretreated lignocellulosic material, which can optionally include the pretreatment solution and/or by-products from the pretreatment process, such as, but not limited to, polyol(s), glycerol residue, acid(s), and products produced from the pretreatment process), such as in amounts from about 0.001% to about 50%, from about 0.01% to about 50%, from about 0.1% to about 50%, from about 1% to about 50%, from about 10% to about 50%, from about 20% to about 50%, from about 30% to about 50%, from about 40% to about 50% by weight of the substrate, or more.

An enzyme composition also can include agents known to those of skill in the art for use in processing lignocellulosic material (e.g., biomass) including, but not limited to, a chlorine, detergent, hypochlorite, hydrogen peroxide, oxalic acid, peracid, pH-regulating agent, trisodium phosphate, sodium chlorite, sodium nitrate, surfactant, urea, buffer(s), and/or water.

Examples of detergents include, but are not limited to, anionic, cationic or neutral detergents such as Nonidet (N)P-40, sodium dodecyl sulfate (SDS), sodium lauryl sulfate (SLS), sulfobetaine, n-octylglucoside, deoxycholate, Triton® X-100 (Dow Chemical Co.; Midland, Mich.) and/or Tween® 20 (ICI Americas, Inc.; Bridgewater, N.J.).

Non-limiting examples of surfactants include a secondary alcohol ethoxylate, a fatty alcohol ethoxylate, a nonylphenol ethoxylate, a phosphate ester of fatty alcohols, a polyoxyethylene ether, a polyethylene glycol, a polyoxyethylenated alkyl phenol, a stearic acid and/or a tridecyl ethoxylate.

Any of the agents can be provided as partially or fully purified. Moreover, any of these agents can be provided in an amount from about 0.001% to about 50%, from about 0.01% to about 50%, from about 0.1% to about 50%, from about 1% to about 50%, from about 10% to about 50%, from about 20% to about 50%, from about 30% to about 50%, from about 40% to about 50% by weight of the substrate, or more.

An enzyme composition of the present invention also can include fungi or other enzyme producing microorganisms, especially ethanologenic and/or lignin-solubilizing microorganisms, that can aid in processing, breaking down, and/or degrading lignocellulosic material. Non-limiting examples of ethanologenic and/or lignin-solubilizing microorganisms include bacteria and yeast. See generally, Burchhardt & Ingram (1992) *Appl. Environ. Microbiol.* 58:1128-1133; Dien et al. (1998) *Enzyme Microb. Tech.* 23:366-371; Keating et al. (2004) *Enzyme Microb. Tech.* 35:242-253; Lawford & Rousseau (1997) *Appl. Biochem. Biotechnol.* 63-65:221-241; *Handbook on Bioethanol: Production and Utilization* (Wyman ed., CRC Press 1996); as well as U.S. Patent Application Publication Nos. 2009/0246841 and 2009/0286293; and U.S. Pat. No. 6,333,181. Such microorganisms can produce enzymes that assist in processing lignocellulosic material including, but not limited to, alcohol dehydrogenase, pyruvate decarboxylase, transaldolase, transketolasepyruvate decarboxylase, xylose reductase, xylitol dehydrogenase or xylose isomerase xylulokinase. In some embodiments of the invention, the ethanologenic and/or lignin-solubilizing microorganisms include, but are not limited to, members of the genera *Candida, Erwinia, Escherichia, Klebsiella, Pichia, Saccharomyces, Streptomyces* and *Zymomonas*. See, e.g., Dien (1998), supra; Ingram & Conway (1988) *Appl. Environ. Microbial.* 54:397-404; Jarboe et al. (2007) *Adv. Biochem. Engin./Biotechnol.* 108:237-261; Keating et al. (2004) *J. Indust. Microbiol. Biotech.* 31:235-244; Keating et al. (2006) *Biotechnol. Bioeng.* 93:1196-1206; Pasti et al. (1990) *Appl. Environ. Microbial.* 56:2213-2218; and Zhang et al. (1995) *Science* 267:240-243.

The methods of the present invention can further comprise contacting (e.g., fermenting) the pretreated lignocellulosic material, optionally including the pretreatment solution and/or by-products from the pretreatment process (e.g., polyol(s), glycerol residue, acid(s), and products produced from the pretreatment process), with a microorganism, including, but not limited to, an ethanologenic bacteria, a yeast or a combination thereof. In some embodiments, the contacting can be at a pH in a range from about 2 to about 9. In further embodiments of the present invention, the pretreated lignocellulosic material can then be processed for the production of fermentable sugars and/or for biofuel (e.g., ethanol) production.

The compositions and methods described herein can be used to process lignocellulosic material (e.g., biomass) to many useful organic chemicals, fuels and products. For example, some commodity and specialty chemicals that can be produced from lignocellulosic material include, but are not limited to, acetone, acetate, butanediol, cis-muconic acid, ethanol, ethylene glycol, furfural, glycerol, glycine, lysine, organic acids (e.g., lactic acid), 1,3-propanediol, polyhydroxyalkanoates, and xylose. Likewise, animal feed and various food/beverages can be produced from lignocellulosic material. See generally, Lynd et al. (1999) *Biotechnol. Prog.* 15:777-793; Philippidis, "Cellulose bioconversion technology" pp 179-212 In: *Handbook on Bioethanol: Production and Utilization*, ed. Wyman (Taylor & Francis 1996); and Ryu & Mandels (1980) *Enz. Microb. Technol.* 2:91-102. Potential co-production benefits extend beyond the synthesis of multiple organic products from fermentable carbohydrate in lignocellulosic material. For example, lignin-rich residues remaining after processing can be converted to lignin-derived chemicals or can be used for power production.

In some embodiments of the present invention, the compositions and/or methods described herein can be used to produce a pulp, such as a high value pulp. The pulp produced using the compositions and/or methods of the present invention can be used for the production of various materials and/or products, such as, but not limited to, paper, textile, and microcrystalline cellulose.

In particular embodiments, the methods of the present invention comprise enzymatically hydrolyzing the pretreated lignocellulosic material to produce a fermentable sugar. "Fermentable sugar," as used herein, refers to oligosaccharides and/or monosaccharides that can be used as a carbon source by a microorganism in a fermentation process. Exemplary fermentable sugars include glucose, xylose, arabinose, galactose, mannose, rhamnose, sucrose, fructose, or any combination thereof.

The fermentable sugars can be converted to useful value-added fermentation products, non-limiting examples of which include amino acids, such as lysine, methionine, tryptophan, threonine, and aspartic acid; vitamins; pharmaceuticals; animal feed supplements; specialty chemicals; chemical feedstocks; plastics; solvents; fuels or other organic polymers; lactic acid; butanol and/or ethanol, including fuel ethanol and/or fuel butanol; organic acids, including citric acid, succinic acid and maleic acid; and/or industrial enzymes, such as proteases, cellulases, amylases, glucanases, lactases, lipases, lyases, oxidoreductases, transferases and xylanases.

In some embodiments of the present invention, after enzymatic hydrolysis of the pretreated lignocellulosic material, the product(s) (e.g., a fermentable sugar, ethanol, butanol, etc.) can be separated from the liquid, slurry, solid or gel. Polyol(s) and/or acid(s) can be collected after separation for use in preheating and/or additional treatment steps (i.e., recycling of the polyol(s) and/or acid(s)).

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

Materials and Methods for Examples 2-13

Bagasse Pretreatment and Sample Analysis:

All bagasse samples in Examples 2-13 were prepared according to the methods described herein with the specific conditions, such as the concentration of the components in the pretreatment solutions and the reaction conditions, provided in the specific Examples 2-13 below.

Air-dried depithed bagasse was ground and the material retained between 0.25 mm and 0.50 mm sieve was collected. One gram (moisture content of 5%) of the bagasse was mixed with 10 grams of the pretreatment solution, (e.g., water, acid catalyst, and glycerol). When glycerol was present in the pretreatment solution, the purity grade of the glycerol was analytical grade (i.e., commercial glycerol) with a water content less than 0.5%. The mixture was stirred at 300 rpm and heated at the indicated temperature for a set time as set forth in each example. After pretreatment, the mixture was vacuum-filtered to produce a filtrate (i.e., hydrolysate) portion and a solid residue portion (i.e., pretreated bagasse). A portion of the filtrate (i.e., hydrolysate) was diluted and neutralized by $Na_2CO_3$ and then analyzed for sugars by high performance liquid chromatography (HPLC) and using a RPM monosaccharide column (Phenomenex). The portion of the hydrolysate that was not neutralized was analyzed for organic acids, 5-hydroxymethylfurfural (HMF), furfural and 3-monochloropropane-1,2-diol (3-MCPD) by HPLC using a Aminex HPX 87H column (Bio-rad). The solid residue (i.e., pretreated bagasse) was washed 4 times with 300 mL of distilled water and then filtered. The washed solid residue was kept at 2° C.-6° C. prior to enzymatic digestibility analysis.

A portion of the solid residue was freeze-dried for composition analysis (e.g., glucan, xylan and lignin) by the Laboratory Analytical Procedure (NREL, 2008). A further portion of the freeze-dried sample was analyzed by Fourier transform infra-red (FTIR) spectroscopy and scanning electron microscopy (SEM).

The effects of various pretreatment conditions on the digestibility of bagasse were examined in the following examples, including (a) acid type, (b) acid concentration, (c) glycerol content, (d) reaction temperature, and (e) pretreatment time.

Glucan/xylan/lignin content in pretreated bagasse residue was calculated based on the following formula:

$$\text{Glucan/xylan/lignin content} = \frac{\text{Total glucan/xylan/lignin in pretreated bagasse residue} \times 100\%}{\text{Dry weight of pretreated bagasse residue}}$$

Glucan/xylan/lignin recovery was calculated based on the following formula:

$$\text{Glucan/xylan/lignin recovery} = \frac{\text{Total glucan/xylan/lignin in pretreated bagasse residue} \times 100\%}{\text{Total glucan/xylan/lignin in untreated bagasse}}$$

Glucose yield in hydrolysate was calculated based on the following formula:

$$\text{Glucose yield} = \frac{\text{Total glucose measured in hydrolysate} \times 100\%}{\text{Total glucan in untreated bagasse} \times 1.111}$$

Xylose yield in hydrolysate was calculated based on the following formula:

$$\text{Xylose yield} = \frac{\text{Total xylose measured in hydrolysate} \times 100\%}{\text{Total xylan in untreated bagasse} \times 1.136}$$

Furfural yield in hydrolysate was calculated based on the following formula:

$$\text{Furfural yield} = \frac{\text{Total furfural measured in hydrolysate} \times 100\%}{\text{Total xylan in untreated bagasse} \times 0.727}$$

HMF yield in hydrolysate was calculated based on the following formula:

$$\text{HMF yield} = \frac{\text{Total HMF measured in hydrolysate} \times 100\%}{\text{Total glucan in untreated bagasse} \times 0.778}$$

Measurement of Enzymatic Digestibility:

Enzymatic hydrolysis was conducted in a 20 mL bottle containing 5 mL of enzyme solution. The enzymatic hydrolysis was carried out at 50° C. for 72 hours. The amount of pretreated bagasse used in each assay contained an equivalent of 2% cellulose loading. The enzyme Accellerase® was used for enzymatic hydrolysis of the pretreated bagasse in an amount of 0.5 mL enzyme per gram pretreated bagasse. Accellerase® is an enzyme mixture containing cellulases and xylanases.

Enzymatic digestibility was calculated based on the amount of glucose released by enzymatic hydrolysis compared to the total glucan in pretreated bagasse before enzymatic hydrolysis.

Digestibility was calculated based on the following formula:

$$\text{Digestibility} = \frac{\text{Total glucan converted to glucose after enzymatic hydrolysis} \times 100\%}{\text{Total glucan in sample}}$$

Example 2

FTIR Data of Untreated Bagasse and Pretreated Bagasse

FIG. 1 shows FTIR spectra of untreated bagasse and bagasse pretreated with either an acid solution or a glycerol/acid/water solution. The bagasse samples were either untreated or pretreated with the acid solution or the glycerol/acid/water solution for 60 minutes at 130° C. The acid solution contained 1.2% HCl and 98.8% water. The glycerol/acid/water solution contained 1.2% HCl, 88.8% glycerol, and 10% water.

The ester bond signal at 1732 $cm^{-1}$ was weaker in the spectrum of the pretreated samples than that of the untreated sample, suggesting that some ester linkages between lignin and the carbohydrates were cleaved during the pretreatment process (Liu et al., 2009).

The peaks at 1515 $cm^{-1}$ and 1605 $cm^{-1}$, which relate to the aromatic skeleton vibrations in lignin (Liu et al., 2009), were present in the pretreated samples, indicating that the pretreatment process did not completely remove lignin. The peaks at 1515 $cm^{-1}$ and 0.1605 $cm^{-1}$ were sharper for the acid pretreated bagasse than those for the untreated bagasse and the glycerol/acid/water pretreated bagasse, which indicates a higher lignin content in the acid pretreated bagasse. This is consistent with the lignin content shown in Table 1.

Sharper absorption peaks occurred at 1425 $cm^{-1}$ and 1460 $cm^{-1}$ for the acid pretreated bagasse, which may be attributed to a higher content of methoxy groups present in the lignin (Guo et al., 2008). Absorbance by the hydroxyl groups occurred in different bands, with a prominent band at 1050 $cm^{-1}$ due to the 1 ry OH group in lignin or the C—OH bending in hemicellulose. Furthermore, a phenolic hydroxyl group band is observable at 1375 $cm^{-1}$. These features are recognized as the common functional groups associated with the structure of lignin (Guo et al., 2008; Li et al., 2009).

Peaks at 1320 $cm^{-1}$ were attributed to C—H vibrations in cellulose and Cl—O vibrations in syringyl derivatives (Zhao et al., 2008). The peak at 1320 $cm^{-1}$ was sharper for the acid pretreated bagasse than for those of the untreated bagasse and the glycerol/acid/water pretreated bagasse, possibly due to higher syringyl lignin content in the acid pretreated bagasse.

The increase in the peak at around 1200 $cm^{-1}$ for both the acid and glycerol/acid pretreated bagasse, suggests an increased contribution from second OH groups (Guo et al., 2008). The peak at 1105 $cm^{-1}$, which refers to the removal of crystalline cellulose, is sharper for the acid pretreated bagasse, and indicates that the acid pretreatment increased the crystallinity of the bagasse (Li et al., 2010). A small sharp band at 898 $cm^{-1}$ is characteristic of β-glycosidic linkages, and demonstrates the presence of predominant β-glycosidic linkages between the sugar units in cellulose and hemicellulose (Liu et al., 2009). The peak at 835 $cm^{-1}$, which belongs to a C—H out of plane vibration in lignin, is sharper in the acid pretreated bagasse indicating higher lignin content in the acid pretreated bagasse (Zhao et al., 2008).

Example 3

SEM of Untreated Bagasse and Pretreated Bagasse

Scanning electron microscopy (SEM) analysis was conducted to study changes in bagasse morphology following various pretreatments. The bagasse samples were either untreated or pretreated with an acid solution or a glycerol/acid/water solution for 60 minutes at 130° C. The acid solution contained 1.2% HCl and 98.8% water. The glycerol/acid/water solution contained 1.2% HCl, 88.8% glycerol, and 10% water.

Figure 2:
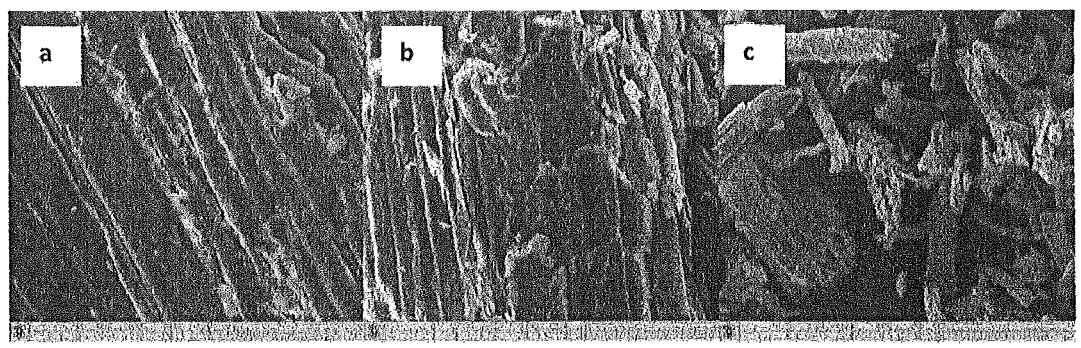
FIG. 2 shows SEM images of (a) untreated bagasse, (b) bagasse pretreated with an acid solution, and (c) bagasse pretreated with a glycerol/acid/water solution. Samples were magnified 1000 times.

As shown in FIG. 2, the untreated bagasse sample exhibited grid and compact fibrils (FIG. 2a), which hinder the ability of the enzymes to access the cellulosic and hemicellulosic components of the bagasse (i.e., the lignocellulosic material) during saccharification. The morphology of bagasse pretreated with the acid solution did not change significantly compared to untreated bagasse (FIG. 2b), although some pores appeared in the acid pretreated bagasse. In contrast, pretreatment with the glycerol/acid/water solution destroyed the rigid structure of bagasse (FIG. 2c). Without being bound to a particular theory, this may be attributed to the removal of hemicellulose and some of the lignin from the bagasse, resulting in the dissociation of the fibrils, increased porosity and increased specific surface area of the material.

Example 4

Effect of Glycerol Concentration in the Pretreatment Solution on the Content, Recovery, and Enzymatic Digestibility of Pretreated Bagasse The effect of varying the amount of glycerol in the glycerol/acid/water solution was examined. The amounts of glycerol and water used in the glycerol/acid/water pretreatment solution, which used 1.2% HCl as the acid catalyst, are given in Table 1. Pretreatment of the bagasse samples with a glycerol/acid/water solution was performed at 130° C. for 60 min. Glycerol/acid/water solutions containing more than 78% glycerol produced a solid residue having greater than 60% glucan and less than 8% xylan and an enzyme digestibility of about 88% or more. Bagasse treated with a glycerol/acid/water solution containing 58.8% glycerol showed lower digestibility than bagasse pretreated with pretreatment solutions having higher amounts of glycerol, but greater digestibility than bagasse treated with only 1.2% HCl (Table 1).

Table 2 shows the components detected in the hydrolysate after pretreatment. The proportion of glucose in the hydrolysate increased with increasing glycerol content. Unexpectedly, 5-hydroxymethylfurfural (HMF), a dehydration product of glucose which is usually produced under acidic pretreatment conditions, was not detected in the hydrolysates. 5-HMF is generally considered to be an undesirable product because it is an inhibitor of microorganism growth.

Xylose is the hydrolysis product of xylan and can be fermented to biochemicals and ethanol by some microorganisms though currently the fermentation efficiency is not commercially economical. Xylose concentration increased in the hydrolysate with decreasing glycerol content in the pretreatment solution and the furfural values obtained were variable. It was expected that a higher concentration of xylose and furfural would be detected in the hydrolysate from pretreatments with high glycerol concentration because solutions with higher glycerol content have higher acidity, and higher acidity generally produces more xylose and furfural. It is therefore likely that some of the furfural and xylose may have been converted to unidentified products. Furfural is generally considered to be an undesirable product because it is an inhibitor of microorganism growth.

Interestingly, the concentration of acetic acid measured in the hydrolysate after pretreatment with the 93.6% glycerol pretreatment solution was less than the amount of acetic acid measured in the hydrolysate after pretreatment with pretreatment solutions containing lower amounts of glycerol. Without being bound to a particular theory, this may be attributable, to a side reaction in which acetic acid is consumed by glycerol through an esterification process. Similarly, acetic acid is generally considered to be an undesirable product because it is an inhibitor of microorganism growth.

It has been reported that glycerol chlorination occurs when HCl is present in glycerol and that chlorination is more efficient in the presence of organic acids, such as acetic acid (Tesser at al., 2007). Glycerol chlorination products include 3-MCPD, 2-monochloropropane-1,2-diol (2-MCPD), 1,3-dichloropropane-2-ol (1,3-DCP) and 1,2-dichloropropane-3-ol (1,2-DCP), with 3-MCPD and 1,3-DCP as the dominant products (Tesser et al., 2007). As shown in Table 2, the amount of 3-MCPD decreased with decreasing glycerol content, suggesting that glycerol loss due to glycerol chlorination is minimized at low glycerol content. Glycerol chlorination products may inhibit enzymatic hydrolysis and yeast fermentation of the hydrolysate obtained after enzymatic digestion.

TABLE 1

Pretreatment of bagasse using a pretreatment solution with 1.2% HCl and various glycerol concentrations at 130° C. for 60 min.

| Glycerol/HCl/water (%) | Content in solid residue (%) | | | Total recovery in solid residue (%) | | | Digestibility (%) |
|---|---|---|---|---|---|---|---|
| | Glucan | Xylan | Lignin | Glucan | Xylan | Lignin | |
| 96.3/1.2/2.5 | 65.5 | 1.3 | 26.4 | 86.7 | 3.2 | 54.9 | 100.0 |
| 88.8/1.2/10.0 | 65.1 | 1.5 | 25.7 | 88.8 | 3.8 | 55.7 | 100.0 |
| 78.8/1.2/20.0 | 62.1 | 7.3 | 26.1 | 89.1 | 19.7 | 60.2 | 87.9 |
| 58.8/1.2/40.0 | 52.7 | 8.9 | 27.8 | 98.3 | 31.2 | 82.4 | 60.3 |
| 0.0/1.2/98.8 | 56.3 | 8.5 | 31.0 | 94.1 | 26.7 | 82.3 | 38.4 |
| Glycerol only | 43.0 | 22.6 | 26.4 | 99.4 | 98.3 | 97.0 | 9.5 |
| Untreated bagasse | 42.9 | 22.8 | 27.0 | 100.0 | 100.0 | 100.0 | 6.9 |

TABLE 2

Composition of hydrolysates obtained after bagasse pretreatment using 1.2% HCl at 130° C. for 60 min at various glycerol contents.

| Glycerol/HCl/water | Concentration in solution after pretreatment (g/kg) | | | | | Yield (%) | | |
|---|---|---|---|---|---|---|---|---|
| (%) | Glucose | Acetic acid | Xylose | Furfural | 3-MCPD | Glucose | Xylose | Furfural |
| 96.3/1.2/2.5 | 1.5 | 3.1 | 1.2 | 0.4 | 11.5 | 3.6 | 4.8 | 2.6 |
| 88.8/1.2/10.0 | 1.3 | 3.6 | 2.2 | 1.1 | 2.2 | 3.2 | 8.8 | 7.7 |
| 78.8/1.2/20.0 | 1.1 | 3.5 | 3.7 | 1.1 | 0.5 | 2.6 | 15.2 | 8.6 |
| 58.8/1.2/40.0 | 0.7 | 3.5 | 7.7 | 0.7 | — | 1.8 | 31.2 | 3.8 |

Example 5

Effect of Pretreatment Temperature on Content, Recovery, and Enzymatic Digestibility of Bagasse Table 3 shows the effect of pretreatment temperature on the enzymatic digestibility of pretreated bagasse. Bagasse samples were pretreated with a solution containing 88.8% glycerol, 10.0% water and 1.2% HCl for 60 minutes. A temperature of 130° C. resulted in the highest amount of glucan obtained after pretreatment, as well as rendering the bagasse more amenable to enzyme hydrolysis. Most of the xylan present in bagasse was removed at 130° C.

TABLE 3

Pretreatment of bagasse using a glycerol/acid/water (88.8%/1.2%/10.0%) solution at 90° C., 110° C. and 130° C. for 60 min.

| Pretreatment temperature | Content in solid residue (%) | | Total recovery in solid residue (%) | | Digestibility (%) |
|---|---|---|---|---|---|
| | Glucan | Xylan | Glucan | Xylan | |
| 90° C. | 47.0 | 12.6 | 92.5 | 39.3 | 40.0 |
| 110° C. | 59.4 | 7.8 | 90.3 | 18.8 | 86.1 |
| 130° C. | 65.1 | 1.5 | 88.8 | 3.2 | 100.0 |
| Untreated bagasse | 42.9 | 27.1 | 100.0 | 100.0 | 6.9 |

Example 6

Effect of Acid Concentration on Content, Recovery, and Enzymatic Digestibility of Bagasse Table 4 shows the effect of HCl concentration in the pretreatment of bagasse and its enzymatic digestibility. Changing the HCl concentration in the pretreatment solution resulted in small changes in the glycerol content, such as from 87.6% to 89.6, since water content in the pretreatment solution was kept at 10%. The small changes in glycerol content did not generate a major impact on the pretreatment process. Each of the bagasse samples were pretreated with a pretreatment solution for 60 minutes at 130° C.

The glucan content in the solid residue was about 60% with each of the acid concentrations used in the study. Xylan recovery in the solid residue was about 32% and 2.7% using a pretreatment solution with 1.2% and 2.4% HCl, respectively. The digestibility of bagasse pretreated with 1.2% HCl and 2.4% HCl reached 100% in a 72 hour enzymatic hydrolysis assay (Table 4).

TABLE 4

Pretreatment solutions with varying concentrations of HCl.

| HCl/glycerol/water (%) | Content in solid residue (%) | | Total recovery in solid residue (%) | | Digestibility (%) |
|---|---|---|---|---|---|
| | Glucan | Xylan | Glucan | Xylan | |
| 0.4/89.6/10.0 | 59.0 | 7.8 | 89.8 | 18.8 | 86.5 |
| 1.2/88.8/10.0 | 65.1 | 1.5 | 88.8 | 3.2 | 100.0 |
| 2.4/87.6/10.0 | 65.7 | 1.6 | 82.1 | 2.7 | 100.0 |
| Untreated bagasse | 42.9 | 27.1 | 100.0 | 100.0 | 6.9 |

Example 7

Effect of Length of Time for Pretreatment on Content, Recovery, and Enzymatic Digestibility of Bagasse Bagasse samples were pretreated for about 15, 30, 60, or 90 minutes at 130° C. with a pretreatment solution comprising 88.8% glycerol, 10% water and 1.2% HCl. As shown in Table 5, a higher proportion of xylan was removed from bagasse as pretreatment time increased. The amount of glucan obtained in the solid residue was over 60% even after 15 min of pretreatment.

The digestibility of bagasse pretreated for 15 min or 30 min reached 88.1% and 96.6%, respectively, using a 72 hour enzymatic hydrolysis assay. Longer pretreatment times resulted in 100% digestibility.

TABLE 5

Pretreatment of bagasse using a glycerol/acid/water (88.8%/1.2%/10%) solution at 130° C. at various times

| Pretreatment time | Content in solid residue (%) | | Total recovery in solid residue (%) | | Digestibility (%) |
|---|---|---|---|---|---|
| | Glucan | Xylan | Glucan | Xylan | |
| 15 min | 61.2 | 7.6 | 89.9 | 17.7 | 88.1 |
| 30 min | 63.3 | 4.9 | 89.2 | 9.2 | 96.6 |
| 60 min | 65.1 | 1.5 | 88.8 | 3.2 | 100.0 |
| 90 min | 65.7 | 1.8 | 87.0 | 3.0 | 100.0 |
| Untreated bagasse | 42.9 | 27.1 | 100.0 | 100.0 | 6.9 |

Example 8

Use of $H_2SO_4$ as the Acid Catalyst in the Pretreatment Solution

Table 6 shows the glucan and xylan content in the solid residue (%) and total recovery in the solid residue (%) after bagasse pretreatment with a glycerol/acid/water pretreatment solution using $H_2SO_4$ as the acid catalyst. The bagasse was treated with the pretreatment solution at 130° C. for 60, 90, or 120 minutes. The amount of glucan in the pretreated bagasse was more than 60% compared to a value of 42.9% for untreated bagasse. The amount of xylan removed from bagasse was more than 80%.

TABLE 6

Pretreatment of bagasse using $H_2SO_4$ as the catalyst in the pretreatment solution.

| $H_2SO_4$/water/glycerol (%) and pretreatment time | Content in solid residue (%) | | Total recovery in solid residue (%) | |
|---|---|---|---|---|
| | Glucan | Xylan | Glucan | Xylan |
| 1.6/10.0/88.4, 60 min | 62.2 | 6.4 | 93.3 | 15.2 |
| 1.6/10.0/88.4, 90 min | 63.5 | 2.5 | 91.4 | 5.8 |
| 1.6/10.0/88.4, 120 min | 63.6 | 3.3 | 89.3 | 7.3 |
| 1.6/20.0/78.4, 90 min | 61.0 | 6.1 | 91.7 | 14.6 |
| 1.6/20.0/78.4, 120 min | 60.3 | 6.0 | 90.9 | 14.3 |
| Untreated bagasse | 42.9 | 27.1 | 100.0 | 100.0 |

Example 9

Use of $FeCl_3$ as the Catalyst in the Pretreatment Solution

Table 7 shows the glucan and xylan content in the solid residue (%) and total recovery in the solid residue (%) after bagasse pretreatment with a pretreatment solution using $FeCl_3$ as the acid catalyst at 130° C. for 60 min. An increase in the glucan content in the pretreated bagasse was achieved using a pretreatment solution with higher $FeCl_3$ concentrations. The presence of 10% water in the glycerol/$FeCl_3$/water pretreatment solutions, resulted in lower glucan content in the solid residue and less digestibility compared to $FeCl_3$/glycerol pretreatment solutions containing no water.

TABLE 7

Pretreatment of bagasse using $FeCl_3$ as the catalyst in the pretreatment solution.

| $FeCl_3$/water/glycerol (%) | Content in solid residue (%) | | Total recovery in solid residue (%) | | Digestibility (%) |
|---|---|---|---|---|---|
| | Glucan | Xylan | Glucan | Xylan | |
| 0.6/0.0/99.4 | 57.2 | 8.4 | 93.0 | 21.6 | 82.0 |
| 1.2/0.0/98.8 | 61.8 | 6.6 | 90.8 | 15.4 | 87.3 |
| 2.4/0.0/97.6 | 65.0 | 4.7 | 90.3 | 10.3 | 91.0 |
| 0.6/10.0/89.4 | 56.8 | 10.1 | 93.2 | 26.3 | 63.3 |
| 1.2/10.0/88.8 | 61.0 | 6.9 | 91.5 | 16.4 | 85.8 |
| 2.4/10.0/87.6 | 64.6 | 5.0 | 91.3 | 11.2 | 89.1 |

Example 10

Effect of Glycerol Concentration in Acid and Soda-Pretreated Bagasse on Enzymatic Hydrolysis The effect of glycerol concentration on the enzymatic hydrolysis of acid and soda-pretreated bagasse was investigated. The acid pretreated bagasse was prepared by pretreatment of the bagasse with a 0.73% $H_2SO_4$ solution at 170° C. for 15 min in a Parr reactor. The soda pretreated bagasse was prepared by pretreatment of the bagasse with a 18% NaOH solution at 170° C. for 40 min in a Pan reactor. The pretreated bagasse was washed 4 times with 300 mL distilled water. After washing the bagasse, the bagasse was filtrated and air-dried. The air-dried bagasse was milled by a cutting grinder to generate bagasse powder for the enzymatic hydrolysis analysis.

The addition of glycerol from 5% to 30% to the enzymatic hydrolysis solution of pretreated bagasse inhibited cellulase hydrolysis in the first 12 hours. The level of inhibition of cellulase activity increased with increasing glycerol concentration during the first 12 hours. However, the cellulose digestibility of the pretreated bagasse in the presence of 5% and 10% glycerol surpassed that without glycerol addition after 24 hours and 72 hours. It is known that glycerol can be used as an enzyme stabilizer for enzymes during freezing storage and thawing processes. Glycerol has also been used to store some enzymes at temperatures above 0° C. (Costa et al 2002). While not wishing to be bound to any particular theory, the results here indicate that glycerol may stabilize cellulase activity over longer periods of time, even though it inhibits hydrolysis during the initial hydrolysis stage.

Example 11

Effect of Glycerol Concentration in Glycerol/Acid/Water Pretreated Bagasse on Enzymatic Hydrolysis The effect of glycerol concentration on the enzymatic hydrolysis of glycerol/acid/water pretreated bagasse was investigated. Bagasse was pretreated with a pretreatment solution containing 1.2% HCl, 88.8% glycerol and 10% water at 130° C. for 60 minutes and was then filtrated. A portion of the pretreated bagasse was washed as described in Example 1 before enzymatic hydrolysis. The other portion of the pretreated bagasse was used directly (i.e., without washing) for enzymatic hydrolysis.

Example 12

Recycling of the Pretreatment Solution

A bagasse sample was pretreated with a fresh batch of pretreatment solution containing 88.8% glycerol, 10% water, and 1.2% HCl. The pretreatment temperature and time for the initial and subsequent pretreatments were 130° C. and 30 min, respectively. After pretreatment, the filtrate/hydrolysate was collected and water was removed by vacuum evaporation at 80° C. to produce a concentrated filtrate. Without adding any additional HCl, the concentrated filtrate was adjusted to a water content of approximately 10% to produce a recycled pretreatment solution. The recycled pretreatment solution was then used to pretreat a fresh bagasse sample. After pretreatment, the filtrate was again collected and the same process was followed for recycling the pretreatment solution. The pretreatment solution was recycled a second and third time and each recycled solution was used to pretreat a fresh bagasse sample. After each pretreatment, the pretreated bagasse was collected, washed and filtrated, as describe in Example 1, before enzymatic hydrolysis.

The digestibility of bagasse after pretreatment using the first recycled solution was 99%. Thus, the first recycled pretreatment solution showed no significant decrease in effectiveness in regards to digestibility compared to the fresh pretreatment solution. The digestibility of bagasse pretreated with the third recycled pretreatment solution remained greater than 92%. While not wishing to be limited by any particular theory, the slight decrease seen in the digestibility of bagasse pretreated with a recycled glycerol solution suggests that the acidity of the pretreatment solution may become weaker after several uses.

Example 13

Two-Step Pretreatment of Bagasse

A two-step pretreatment process for bagasse was utilized to determine the effect on the production of inhibitory components compared to a one-step pretreatment. In the first step of the two-step pretreatment process, a dilute acid was used to pretreat bagasse (i.e., pre-pretreatment). The dilute acid pre-pretreatment removes most of the xylan in bagasse. In the second step of the two-step pretreatment process, a glycerol/acid/water pretreatment solution was used to further pretreat the bagasse. Inhibitory components, such as furfural and acetic acid, were significantly reduced in the two-step pretreatment process compared to the one-step pretreatment of the bagasse with the glycerol/acid/water pretreatment solution only.

Specifically, for the first step of the two-step pretreatment process, 1 gram of bagasse was pre-pretreated with 10 grams of a dilute acid solution containing 1.2% HCl at 130° C. for 1 hour. The pre-pretreated bagasse was filtrated and washed as described in Example 1. Then, the pre-pretreated bagasse was air-dried. Several batches of pre-pretreated bagasse were prepared using the first step of the two-step pretreatment process to obtain sufficient pre-pretreated biomass for the second step of the two-step pretreatment process.

For the second step of the two-step pretreatment process, 1.0 gram of the air-dried pre-pretreated bagasse was pretreated with 10 grams of a glycerol/acid/water pretreatment solution containing 88.8% glycerol, 1.2% HCL, and 10.0% water at 130° C. for 1 hour. The pretreated bagasse samples were then washed and filtrated, as described in Example 1, before enzymatic hydrolysis.

Example 14

Materials and Methods

Sugarcane bagasse was used as a model lignocellulosic biomass and was collected from Racecourse sugar mill (Mackay Sugar Limited, Australia) in Mackay, Australia. Sugarcane bagasse was washed in the sugar mill using hot water (90° C.) and the residual sugar attached on bagasse was negligible. The sugarcane bagasse was air-dried, depithed and grinded by a cutter grinder (Retsch® SM100, Retsch GmBH, Germany). The milled bagasse was screened and bagasse having particle sizes of 250-500 μm was collected and stored for experiment. The moisture of the bagasse powder was 6.9%. Glycerol was purchased from Biolab Scientific Pty Ltd (Australia). Ethylene glycol and 1,2-propanediol were purchased from Sigma-Aldrich company (Australia). All solvents used in this study were analytical grade. Accellerase™ 1000 (Batch no. 1600877126) was a Danisco product (Genencor Division, Danisco Inc., US) and was purchased through Enzymes Solutions Pty. Ltd (Australia). The filter paper activity of Accellerase™ 1000 was approximate 40 FPU/mL. All the chemicals used in this study were analytic reagents.

Pretreatment Experiment

Polyol solution which contained a required amount of HCl and water was transferred into a 50 mL glass flask. A magnetic stirrer was placed into the flask. 4.30 g bagasse (4.0 g dry biomass) was transferred into the flask and mixed well. The ratio of liquid to solid was 10:1 (weight to weight). The pretreatment conditions are shown in Table 8. The flask was sealed with a lid avoiding water loss and immersed to a silicone oil bath, which was preheated to the required temperature. The heating element was equipped with a magnetic stirring device (Ika Labortechnik, Germany). The pretreatment was carried out under magnetic stirring (500 rpm) for a required time. After pretreatment, the pretreatment solution was transferred to a beaker and 20 mL water was added. The solution was mixed well and then filtered through a filter paper (Whatman 541) to collect solid residue. The filtrate was collected and stored in freezer for further analysis. The solid residue was washed with 900 mL distilled water (3×300 mL/wash). The washed solid residue was filtered and collected. The filtered solid residue was freeze-dried and stored for compositional analysis and enzymatic hydrolysis. Compositional analysis of bagasse and pretreated bagasse samples was conducted according to a standard procedure developed by National Renewable Energy Laboratory (NREL, US) (Sluiter et al., 2008).

TABLE 8

Pretreatment conditions.

| Polyol | Solvent composition (%) | | | Temperature (° C.) | Time (min) | Condition label |
| --- | --- | --- | --- | --- | --- | --- |
| | HCl | water | polyol | | | |
| glycerol | 1.2 | 10.0 | 88.8 | 130 | 30 | Gly-30 |
| | 1.2 | 10.0 | 88.8 | 130 | 60 | Gly-60 |
| | 0.0 | 0.7* | 99.3 | 130 | 60 | Gly-60, no acid |
| ethylene glycol | 1.2 | 10.0 | 88.8 | 130 | 30 | EG-30 |
| | 1.2 | 10.0 | 88.8 | 130 | 60 | EG-60 |
| | 0.0 | 0.7* | 99.3 | 130 | 60 | EG-60, no acid |
| 1,2-propanediol | 1.2 | 10.0 | 88.8 | 130 | 30 | Diol-30 |
| | 1.2 | 10.0 | 88.8 | 130 | 60 | Diol-60 |
| | 0.0 | 0.7* | 99.3 | 130 | 60 | Diol-60, no acid |
| Water | 1.2 | 98.8 | 0.0 | 130 | 60 | Acid in water |

*The water came from the sugarcane bagasse.

Enzymatic Hydrolysis

Enzymatic hydrolysis was carried out in a 20 mL glass vial containing 5 g solution. The cellulose loading of 2% was used based on cellulose content in bagasse sample. The reaction solution contained 0.05 M citrate buffer to maintain pH at 4.8 and 0.02% sodium azide to prevent the growth of microorganisms. The dosage of Accellerase for enzymatic hydrolysis was 0.5 mL Accellerase/g cellulose (approximate 20 FPU/g cellulose) unless otherwise stated. The reaction was carried out at 50° C. in a rotary incubator (Ratek OM 11 Orbital Mixer, Australia) with shaking speed of 150 rpm. The sampling time was 0 h, 6 h, 12 h, 24 h, 48 h and 72 h. The sampling volume was 0.2 mL using a cut-off pipette tip. After sampling, the sample was sealed and incubated for 5 min in a boiling water bath to denature the cellulase. The sample was then centrifuged at 10,000 rpm for 5 min, 0.1 mL supernatant was diluted 10 times by de-ionized water.

The diluted sample was filtered through 0.22 μm disk filter before HPLC analysis. All the enzymatic hydrolysis experiments were conducted in duplicate and the data showed in this study were the means.

HPLC Analysis

HPLC was used to analyze the chemicals generated in this study. A Bio-Rad Aminex HPX-87H column and Waters refractive index detector were used to detect and quantify organic acids (acetic acid, levulinic acid, etc.), 5-hydroxymethylfurfural (HMF) and furfural. The mobile phase was 5 mM $H_2SO_4$ at a flow rate of 0.6 mL/min. The temperature for the column was 85° C. A Shodex SP 810 carbohydrate column was used to determine the sugars generated in the compositional analysis and enzymatic hydrolysis. The temperature for both columns was 85° C. and the mobile phase was water with a flow rate of 0.5 ml/min. The samples (except the enzymatic hydrolysis samples) were neutralized by $CaCO_3$ before running through the columns.

Calculation

Glucan (xylan) recovery was calculated based on the following equation:

$$\text{Glucan(xylan)recovery in solid residue} = \frac{\text{Total glucan(xylan)in pretreated bagasse residue} \times 100\%}{\text{Total glucan(xyaln)in untreated bagasse}} \quad (1)$$

Glucan digestibility was calculated based on the following equation:

$$\text{Digestibility} = \frac{\text{Total glucose in enzymatic hydrolysis} \times 0.9 \times 100\%}{\text{Total glucan in sample}} \quad (2)$$

Total glucose yield after enzymatic hydrolysis was calculated based on the following equation:

$$\text{Total glucose yield} = \frac{\text{Total glucose in enzymatic hydrolysis} \times 0.9 \times 100\%}{\text{Total glucan in untreated bagasse}} \quad (3)$$

The yield of glucose (xylose and furfural) detected in pretreatment hydrolysate on bagasse was calculated based on the following equation:

$$\text{Yield on bagasse} = \frac{\text{Total glucose(xylose or furfural) in pretreatment hydrolysate} \times 100\%}{\text{Untreated bagasse weight}} \quad (4)$$

The yield of glucose (xylose and furfural) detected in pretreatment hydroysate on initial glucan (xylan) was calculated based on the following equations:

$$\text{Glucose yield} = \frac{\text{Total glucose in pretreatment hydrolysate} \times 0.9 \times 100\%}{\text{Total glucan in untreated bagasse weight}} \quad (5)$$

$$\text{Xylose yield} = \frac{\text{Total xylose in pretreatment hydrolysate} \times 0.88 \times 100\%}{\text{Total xylan in untreated bagasse weight}} \quad (6)$$

$$\text{Furfural yield} = \frac{\text{Total furfural in pretreatment hydrolysate} \times 1.375 \times 100\%}{\text{Total xylan in untreated bagasse weight}} \quad (7)$$

Results and Discussion

Sugarcane Bagasse Pretreatment

Pretreatment of sugarcane bagasse was conducted at 130° C. As shown in Table 9, pretreatment polyols without water and acid catalyst only caused slight changes in glucan, xylan and lignin compositions in solid residue compared to untreated bagasse. All the pretreatments retained over 90% glucan. Dilute acid pretreatment at 130° C. for 60 min removed 73% xylan and only 18% lignin (corresponding to xylan recovery of 27% and lignin recovery of 82%). Pretreatment of sugarcane bagasse for 30-60 min by aqueous glycerol containing acid catalyst removed 89-96% xylan and 40-44% lignin (corresponding to xylan recovery of 4-11% and lignin recovery of 56-60%). The glucan content in bagasse pretreated by acidic glycerol was between 63-65%.

TABLE 9

Effect of pretreatment conditions on biomass composition and recovery.

| | Content in solid residue (%) | | | Recovery in solid residue (%) | | |
|---|---|---|---|---|---|---|
| Conditions | Glucan | Xylan | Lignin | Glucan | Xylan | Lignin |
| Gly-30 | 63.3 | 4.9 | 26.2 | 91.2 | 11.2 | 60.0 |
| Gly-60 | 65.1 | 1.5 | 25.7 | 90.6 | 3.9 | 55.7 |
| Gly-60, no acid | 43.0 | 22.6 | 25.6 | 97.0 | 95.9 | 91.8 |
| EG-30 | 76.0 | 4.4 | 16.4 | 94.7 | 10.6 | 31.3 |
| EG-60 | 78.3 | 2.6 | 16.3 | 93.9 | 5.9 | 29.6 |
| EG-60, no acid | 42.8 | 22.3 | 27.0 | 97.3 | 96.4 | 93.4 |
| Diol-30 | 79.3 | 5.8 | 12.7 | 94.2 | 13.1 | 22.9 |
| Diol-60 | 81.9 | 2.9 | 10.3 | 92.6 | 6.1 | 17.7 |
| Diol-60, no acid | 43.0 | 22.5 | 26.8 | 97.9 | 97.4 | 92.8 |
| Acid in water | 56.3 | 8.5 | 31.0 | 94.1 | 26.7 | 82.3 |
| Untreated bagasse | 42.9 | 22.8 | 27.0 | 100.0 | 100.0 | 100.0 |

Pretreatment of bagasse by both ethylene glycol and 1,2-propanediol solutions containing acid removed similar amounts of xylan but high amounts of lignin compared to glycerol pretreatment. 1,2-propanediol pretreatment for only 30 min removed up to 77% lignin (corresponding to lignin recovery of 23%) and extension of pretreatment time to 60 min removed further about 5% lignin. Ethylene glycol pretreatment for 30-60 min removed ~30% lignin, which was 8-13% lower than that by 1,2-propanediol pretreatment. The glucan content in bagasse pretreated by 1,2-propanediol improved to 79% for 30 min pretreatment and 82% for 60 min pretreatment, followed by 76%-78% in bagasse pretreated by ethylene glycol for 30-60 min. The glucan content in bagasse pretreated by both ethylene glycol and 1,2-propanediol was 13-16% higher than that in bagasse pretreated by glycerol.

Enzymatic Hydrolysis of Pretreated Bagasse

Figure 3:
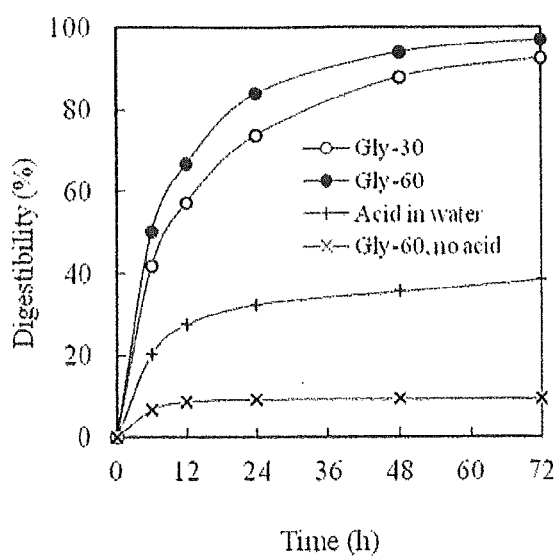
FIG. 3 shows graphs of the kinetics of enzymatic hydrolysis of bagasse pretreated with pretreatment solutions comprising (a) glycerol, (b) ethylene glycol, and (c) 1,2-propanediol.
Figure 3:
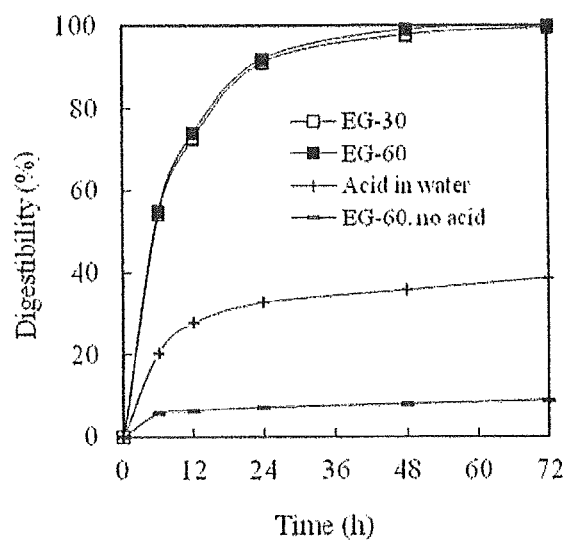
Figure 3:
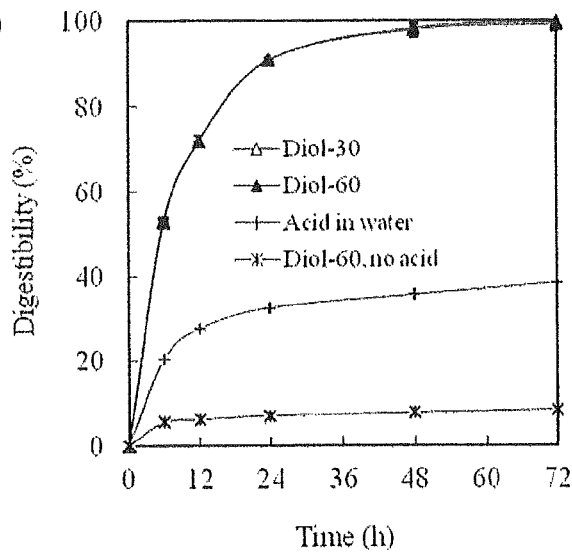

The pretreated bagasse was further enzymatic hydrolyzed with a cellulase loading of 20 FPU/g glucan. As shown in FIG. 3, pretreatment with all three aqueous polyol solutions containing 1.2% HCl improved glucan digestibility significantly compared to pretreatment with water containing 1.2% HCl and polyols without water and acid catalyst. As shown in Table 10 and FIG. 3, the digestibility of bagasse pretreated with polyols without water and acid catalyst was very low, 8-10%. Pretreatment with water containing 1.2% HCl only improved glucan digestibility to 38.4%.

TABLE 10

Glucan digestibility and total glucose yield.

| Conditions | Glucan digestibility (%) | | Total glucose yield (%) | |
|---|---|---|---|---|
| | 24 h | 72 h | 24 h | 72 h |
| Gly-30 | 73.7 | 92.6 | 67.2 | 84.5 |
| Gly-60 | 83.9 | 97.1 | 76.0 | 88.0 |
| Gly-60, no acid | 9.3 | 9.5 | 9.0 | 9.2 |
| EG-30 | 91.0 | 99.4 | 86.2 | 94.1 |
| EG-60 | 91.8 | 99.8 | 86.2 | 93.7 |
| EG-60, no acid | 7.0 | 8.7 | 6.8 | 8.5 |
| Diol-30 | 91.0 | 99.2 | 85.7 | 93.4 |
| Diol-60 | 90.9 | 99.7 | 84.2 | 92.4 |
| Diol-60, no acid | 6.9 | 8.3 | 6.8 | 8.1 |
| Acid in water | 38.4 | 38.4 | 36.1 | 36.1 |

Pretreatment by acidic glycerol solution for 30 min and 60 min improved glucan digestibility to 92.6% and 97.1%. The 24 h digestibilities were 74% and 84% respectively for bagasse pretreated for 30 min and 60 min. The kinetic curves of enzymatic hydrolysis of bagasse pretreated for 30 min and 60 min by both ethylene glycol and 1,2-propanediol were almost identical (FIGS. 3b and 3c, respectively). The 72 h digestibilities for bagasse pretreated for 30 min and 60 min by both ethylene glycol and 1,2-propanediol solutions were more than 99%. The 24 h digestibilities reached 91% for bagasse pretreated by ethylene glycol and 1,2-propanediol solutions.

The 72 h and 24 h total glucose yields (considering the glucan recovery in solid residues) for bagasse pretreated with both ethylene glycol and 1,2-propanediols were 92-94% and 84-86% respectively, which were higher than those for bagasse pretreated with glycerol solutions. All the glucose yields for bagasse pretreated with all the polyols were significantly higher than those for bagasse pretreated with water containing dilute acid and polyol solutions without water and acid catalyst.

Effect of Soda Wash

Without being limited to any particular theory, it is believed that the presence of lignin can form a physical barrier for preventing cellulase access to cellulose and non-productively bind cellulases, which reduce the efficiency of enzymatic hydrolysis (Gilkes et al., 2005). Therefore, removal of lignin could improve enzymatic hydrolysis.

Effect of Soda Wash on Biomass Composition 0.2% NaOH solution (pH 12.3) was used to wash bagasse pretreated for 60 min with polyol solutions. As shown in Table 11, dilute soda wash further decreased the lignin content in all pretreated bagasse. The lignin content in bagasse pretreated by both ethylene glycol and 1,2-propanediol solutions was reduced to less than 5% after soda wash. However, the bagasse pretreated by glycerol solution, the lignin content was still significantly high (19.1%) after soda wash. The glucan content in bagasse pretreated by both ethylene glycol and 1,2-propanediol solutions was improved from 78-82% before soda wash to 91-92% after wash. In contrast, soda wash only improved glucan content in bagasse pretreated by glycerol solution to 72%. The lignin removal by soda wash for sugarcane bagasse pretreated by ethylene glycol and 1,2-propanediol solutions was more readily than pretreated by glycerol solution.

TABLE 11

Effect of dilute soda wash on biomass composition.

| Pretreatment conditions | Soda wash | Content in solid residue (%) | | |
|---|---|---|---|---|
| | | Glucan | Xylan | Lignin |
| Gly-60 | No | 65.1 | 1.5 | 25.7 |
| | Yes | 72.4 | 1.7 | 19.1 |
| EG-60 | No | 78.3 | 2.6 | 16.3 |
| | Yes | 91.1 | 1.7 | 4.8 |
| Diol-60 | No | 81.9 | 2.9 | 10.3 |
| | Yes | 91.7 | 1.9 | 3.6 |

It is believed that most lignin seals and structures were ruptured in pretreatment by ethylene glycol and 1,2-propanediol. The ruptured lignin condensed on biomass particle surface after pretreatment, which could be dissolved in soda solution readily. However, many linkages between lignin and cellulose or the structures of significant amount of lignin were not ruptures in glycerol pretreatment. Therefore, dilute soda wash could not dissolve the residual lignin effectively.

Effect of Soda Wash on Enzymatic Hydrolysis

Figure 4:
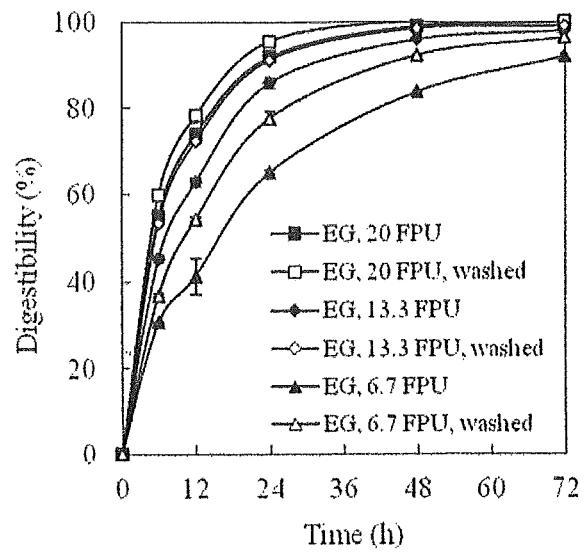
FIG. 4 shows the effect of lignin removal by soda wash on enzymatic hydrolysis of bagasse pretreated with pretreatment solutions comprising (a) ethylene glycol solution and (b) 1,2-propanediol solution.
Figure 4:
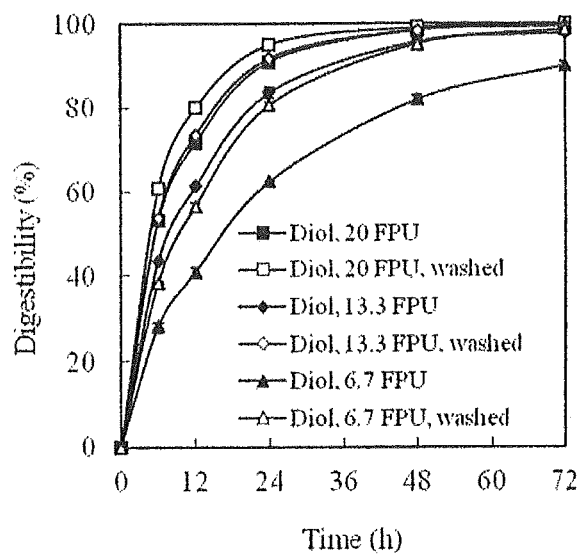

The effects of soda wash on enzymatic hydrolysis were further investigated with loading different amount of cellulases (6.7-20 FPU/g glucan). As shown in FIG. 4, lignin removal by soda wash significantly improved enzymatic hydrolysis of bagasse pretreated by both ethylene glycol and 1,2-propanediol solutions at a low cellulase loading of 6.7 FPU/g glucan. Table 12 shows the 24 h and 72 h digestibilities for pretreated bagasse with or without soda wash. The 24 h digestibilities at a cellulase loading of only 6.7 FPU/g glucan for bagasse pretreated with ethylene glycol and 1,2-propanediol solutions with soda wash were 77.6% and 80.0% respectively, 19.2% and 28.0% higher than those for bagasse without soda wash. The 24 h digestibilities at a cellulase loading of 13.3 FPU/g glucan for bagasse with soda wash were comparable to those at a cellulase loading of 20.0 FPU/g glucan for bagasse without soda wash. Therefore, without being bound to any particular theory, lignin removal by soda wash of bagasse pretreated by polyols could improve enzymatic hydrolysis and also reduce the cellulase loading.

In a previous study, up to 1.0% soda solution was used to remove lignin present in the steam exploded Douglas-fur biomass, which reduced lignin content about 7% and increase glucose conversion about 30% (Gilkes et al., 2005). Our results indicate that residual lignin may be more readily removed from biomass pretreated by ethylene glycol and 1,2-propanediol with low soda concentration (0.2% NaOH) than by steam explosion.

TABLE 12

Effect of lignin removal by soda wash on glucan digestibility at different cellulase loadings.

| Polyol solutions | Cellulase loading (FPU/g gluon) | Digestibility (unwashed, %) | | Digestibility (washed, %) | | Improvement (%) | |
|---|---|---|---|---|---|---|---|
| | | 24 h | 72 h | 24 h | 72 h | 24 h | 72 h |
| EG | 20 | 91.8 | 99.8 | 95.5 | 100.0 | 4.0 | 0.2 |
| | 13.3 | 85.9 | 97.9 | 91.2 | 99.0 | 6.2 | 1.1 |
| | 6.7 | 65.1 | 91.9 | 77.6 | 96.2 | 19.2 | 4.7 |
| Diol | 20 | 90.9 | 99.7 | 95.1 | 100.0 | 4.6 | 0.3 |
| | 13.3 | 83.6 | 97.6 | 91.8 | 99.3 | 9.8 | 1.7 |
| | 6.7 | 62.5 | 90.0 | 80.0 | 98.4 | 28.0 | 9.3 |

Three low cost and high boiling-point polyols were studied for pretreatment of sugarcane bagasse at low temperature (130° C.). Pretreatment for 30-60 min by aqueous and acidic ethylene glycol and 1,2-propanediol solutions (containing 10% water and 1.2% HCl) removed much more lignin from bagasse than that by glycerol pretreatment. The digestibility and total glucose yield reached over 99% and 92% respectively for bagasse pretreated by both ethylene glycol and 1,2-propanediol solutions. Dilute soda (0.2% NaOH) at room temperature wash further decreased the lignin content in pretreated bagasse and resulted in significant improvement of enzymatic hydrolysis at low cellulase loading.

Example 15

Comparison of Processes Used to Treat Sugarcane Bagasse

Figure 5:
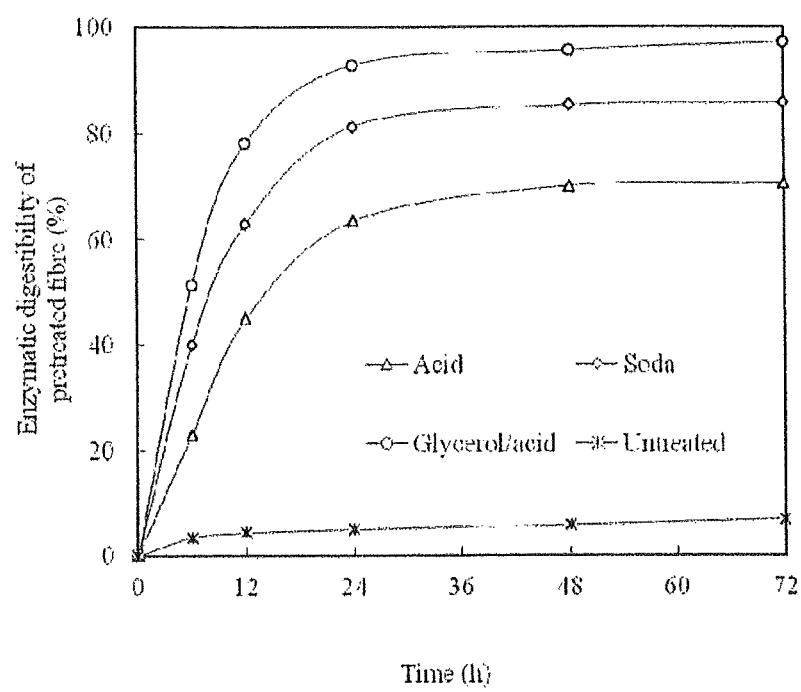
FIG. 5 shows a comparison of dilute acid treatment, caustic soda treatment, and acid-catalyzed aqueous glycerol pretreatment of sugarcane bagasse as well as untreated sugarcane bagasse.

Samples of sugarcane bagasse were separately treated with a dilute acid, a caustic soda, and an acid-catalyzed aqueous glycerol pretreatment solution and compared as shown in FIG. 5. The treatment with the dilute acid comprised treating 1.0 kg of bagasse with 0.73% $H_2SO_4$ in liquid at 170° C. for 15 minutes in a Parr Reactor. The treatment with caustic soda comprised treating 1.0 kg of bagasse with 3.0% NaOH in liquid (14% $Na_2O$ on fiber) at 170° C. for 45 minutes in a Parr Reactor. The acid-catalyzed aqueous glycerol pretreatment comprised treating 4 g of bagasse with a pretreatment solution comprising 1.2% HCl, 10% water, and 88.8% glycerol at 130° C. for 60 minutes.

Example 16

Process for the Conversion of Bagasse into Ethanol and Other Co-Products

Figure 6:
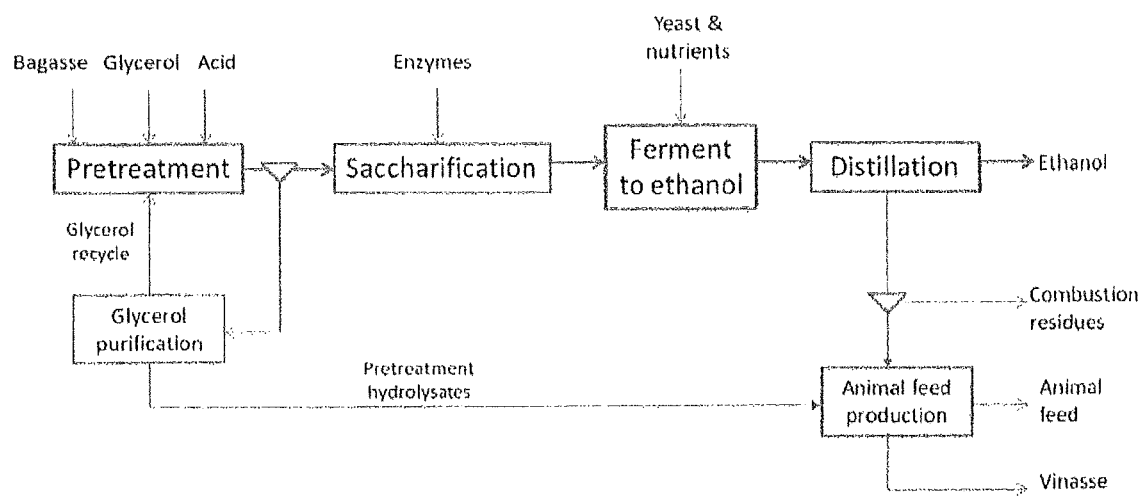
FIG. 6 shows a schematic of an acid-catalyzed aqueous glycerol pretreatment biorefinery process.

FIG. 6 shows a process for converting bagasse into ethanol and other co-products using an acid-catalyzed aqueous glycerol pretreatment process. Raw bagasse (e.g., bagasse with 50% moisture) is pretreated with a pretreatment solution comprising glycerol in the presence of an acid catalyst (e.g., sulphuric acid or hydrochloric acid). The solid residue obtained after pretreatment is enzymatically hydrolyzed using enzymes, such as microbially produced cellulolytic enzymes, and the material is anaerobically fermented with yeast, such as *Saccharomyces cerevisiae*, into ethanol. Residual glycerol and unfermented pentoses from the process stream undergo aerobic fermentation to produce a dried animal feed product.

The pretreatment liquor (containing principally glycerol, lignin and pentoses) is separated from the solid residue at moderate efficiency and the pretreatment liquor undergoes a purification process to concentrate and purify the glycerol prior to recycling and reuse in pretreatment. Glycerol purification can comprise evaporation (to remove water) followed by vacuum distillation of the glycerol. The liquor residue from the purification stage (containing principally lignin and pentoses) is processed for animal feed production.

The ethanol product is distilled and dehydrated to produce fuel grade anhydrous ethanol. The solid residues from distillation (containing principally lignin) can be sold to the sugar factory for combustion for process energy. The liquid residue from distillation and animal feed production (vinasse) can be recycled to farm land where it attracts value as a soil conditioner and fertilizer.

Example 17

Pilot plant experiments were carried out by pretreating sugarcane bagasse with an acid catalyzed aqueous glycerol pretreatment solution using HCl as the acid catalyst. The moisture of the sugarcane bagasse was approximately 50%. A total amount of 20 kg raw sugarcane bagasse (approximately 10 kg dry fibre) was used for each experiment. The general procedure for the pretreatment experiments was as follows:

1. Weigh out the required amount of sugarcane bagasse for the experiment;
2. Dilute the required quantity of HCl in 5-8 kg of water or glycerol and mix evenly through the bagasse;
3. Preheat the reactor to 5° C. above reaction temperature for 20 min;
4. Load the sugarcane bagasse into the reactor through the biomass feeding system and the linear weighing machine. Record the actual weight of sugarcane bagasse loaded into the reactor;
5. Preheat the glycerol in the chemical feed tank to approximately 100° C. and add the required quantity of glycerol into the pretreatment reactor;
6. Heat the reactor to the pre-hydrolysis reaction temperature with direct injection steam and hold at this temperature for the pre-hydrolysis reaction time;
7. After the pre-hydrolysis reaction time has been achieved, shut off the steam supply, and press the material to separate the hydrolysate from the solid residue. Drain hydrolysate to the hydrolysate tank;
8. Empty the hydrolysate tank and sample the hydrolysate. Record the volume or weight of hydrolysate collected;
9. Where a wash stage is required, add the required amount of wash water, heat to the wash temperature with direct injection steam and hold for the wash time. Following the wash, press the material again to separate the wash liquor from the solid residue. The wash liquor drains to the hydrolysate tank and is again sampled. Record the volume or weight of wash liquor collected;
10. Cool the reactor, open the reactor and sub-sample the pre-hydrolysis solid residue if required. Record the weight of sample collected;
11. Preheat vertical reactor to 200° C. for approximately 5 min.
12. Drop the remaining contents of the pre-hydrolysis reactor into the vertical reactor (steam explosion reactor designed by Andritz Inc, NY);
13. Heat the vertical reactor to the vertical reactor temperature and hold for the reaction time;
14. Once the reaction time has been achieved, raise the reactor to the steam explosion pressure and then immediately open the blow valve to expel the material into the solid residue blow tank. Collect and sub-sample the steam exploded solid residue. Record the weight of the steam exploded solid residue collected;

15. Sub-sample the hydrolysate fibre, pre-hydrolysis chamber residual fibre and steam exploded solid residue fibre.

Table 13 shows the experimental conditions used in the pilot plant experiments.

resulted in significant biomass carbonization. No biomass carbonization was evident in the laboratory experiments under the same conditions.

As shown in Table 14, the water concentrations in pretreatment hydrolysates were 32-44%, significantly higher than the optimized values (≤20%) obtained from laboratory experiments. As expected, water concentration varied with the pre-hydrolysis reaction temperature and reaction time. Higher pre-hydrolysis reaction temperatures and longer times led to higher water concentrations in the hydrolysate.

TABLE 13

Experimental conditions for pilot plant experiments.

| # | Pretreatment chemicals | Liquid to solid ratio | Glycerol conc % solution | Water conc % solution | HCl conc % solution | % on dry fibre | Reaction temperature °C | Reaction time, min | Steam explosion? |
|---|---|---|---|---|---|---|---|---|---|
| 1 | glycerol only | 6 | 80.0 | 20.0 | 0.0 | 0.0 | 130 | 15 | No |
| 2 | water-HCl | 6 | 0.0 | 99.6 | 0.4 | 2.4 | 110 | 15 | |
| 3 | glycerol-HCl | 6 | 79.6 | 20.0 | 0.4 | 2.4 | 110 | 15 | |
| 4 | water-HCl | 6 | 0.0 | 99.6 | 0.4 | 2.4 | 110 | 60 | |
| 5 | glycerol-HCl | 6 | 79.6 | 20.0 | 0.4 | 2.4 | 110 | 60 | |
| 6 | water-HCl | 6 | 0.0 | 99.6 | 0.4 | 2.4 | 110 | 60 | Yes, |
| 7 | glycetol-HCl | 6 | 79.6 | 20.0 | 0.4 | 2.4 | 110 | 60 | 170° C. |
| 8 | water-HCl | 6 | 0.0 | 98.8 | 1.2 | 7.2 | 110 | 15 | No |
| 9 | glycerol-HCl | 6 | 78.8 | 20.0 | 1.2 | 7.2 | 110 | 15 | |
| 10 | water-HCl | 6 | 0.0 | 99.6 | 0.4 | 2.4 | 130 | 15 | |
| 11 | glycerol-HCl | 6 | 79.6 | 20.0 | 0.4 | 2.4 | 130 | 15 | |
| 12 | water-HCl | 6 | 0.0 | 98.8 | 1.2 | 7.2 | 130 | 15 | |
| 13 | glycerol-HCl | 6 | 78.8 | 20.0 | 1.2 | 7.2 | 130 | 15 | |

Following pretreatment, solid residue and hydrolysate samples were collected and stored in a refrigerator (<4° C.) for further analysis. The solid residue samples were sub-sampled and the sub-samples were washed with copious amounts of water to remove soluble materials. These washed solid residue samples were analyzed for composition and glucan enzymatic digestibility. The compositional analyses were conducted according to National Renewable Energy Laboratory (NREL) procedures.

The glucan digestibility was analyzed using 100 g solution in a 250 mL shaker flask. The solution contained 2% glucan, approximately 20 FPU cellulase/g glucan (Accellerase 1000 L, Genencor), and 0.05 M citrate buffer to maintain pH at 4.8. The hydrolysis temperature was maintained at 50° C. and the shaking speed was 150 rpm.

Hydrolysate samples were analyzed for organic acid (furfural, 5-HMF, formic acid and levulinic acid) and chlorohydrin (3-MCPD) concentrations. Formic acid and levulinic acid concentrations were low (less than 0.1 g/L) and are not reported.

Results

Laboratory scale experiments suggested that acid catalyzed aqueous glycerol pretreatments with a high water content (>20%) led to poor glucan digestibility and, as a result, it was planned to limit the total reaction water (including water in bagasse and added water) to 20% in the pilot plant scale experiments. However, for the pilot plant scale experiments, with the pre-hydrolysis reactor heated by direct steam injection, the addition of extra water into the pretreatment solution during the reaction was unavoidable. In addition, pilot plant experiments in the pretreatment reactor at 130° C. with glycerol or water solutions containing 1.2% HCl (Experiment numbers 12 and 13, Table 13)

TABLE 14

Water concentration in hydrolysates.

| Pretreatment condition | Water concentration in pretreatment hydrolysate (%) |
|---|---|
| 0.4% HCl in glycerol, 110° C., 15 min | 32 |
| 1.2% HCl in glycerol, 110° C., 15 min | 33 |
| 0.4% HCl in glycerol, 130° C., 15 min | 40 |
| 0.4% HCl in water, 110° C., 60 min | 44 |

Table 15 shows the compositional analysis of the solid residue samples from pretreatment and the 72 h glucan digestibilities from enzymatic hydrolysis. As shown in Table 15, lower lignin contents and higher xylan concentrations were measured in the solid residues from bagasse pretreated by glycerol/acid solutions than in the solid residues from bagasse preheated by water/acid solutions. The high ash concentrations of all samples were the result of the use of bagasse directly from the sugar factory which contained significant quantities of dirt.

TABLE 15

Compositional and enzymatic digestibility of solid residue samples.

| Pretreatment conditions | Content in solid residue (%) | | | | 72 h glucan digestibility (%) |
|---|---|---|---|---|---|
| | Glucan | Xylan | Lignin | Ash | |
| 0.4% HCl in water, 110° C., 15 min | 53.1 | 3.0 | 31.7 | 6.4 | 57.7 |
| 0.4% HCl in glycerol, 110° C., 15 min | 54.5 | 6.4 | 25.4 | 6.9 | 79.2 |
| 1.2% HCl in water, 110° C. 15 min | 53.1 | 0.9 | 30.8 | 6.8 | 66.3 |
| 1.2% HCl in glycerol, 110° C., 15 min | 54.7 | 4.1 | 27.0 | 7.1 | '80.0 |
| 0.4% HCl in water, 130° C., 15 min | 54.1 | 1.5 | 31.8 | 6.4 | 65.4 |
| 0.4% HCl in glycerol, 130° C., 15 min | 54.2 | 3.2 | 26.5 | 8.4 | 90.4 |
| 0.4% HCl in water, 110° C., 60 min | 52.0 | 1.4 | 31.7 | 9.6 | 63.2 |
| 0.4% HCl in glycerol, 110° C., 60 min | 56.5 | 4.5 | 26.2 | 6.7 | 84.6 |
| 0.4% HCl in water, 110° C., 60 min, exploded | 51.6 | 1.2 | 31.7 | 9.6 | 67.2 |
| 0.4% HCl in glycerol, 110° C., 60 rain, exploded | 54.1 | 1.7 | 27.5 | 11.3 | 94.8 |
| glycerol, 130° C., 15 min | 40.5 | 20.7 | 26.3 | 3.8 | 7.8 |

Glucan digestibilities (72 h) of the solid residues from bagasse pretreated by glycerol/acid solutions were higher than those pretreated by water/acid solutions at the same pretreatment temperature and time. Increases in either pretreatment time or pretreatment temperature resulted in improved glucan digestibilities. Pretreatment at 130° C. with glycerol solution containing 0.4% HCl for 15 min resulted in the highest glucan digestibility of non-steam exploded materials of 90.4%, followed by a glucan digestibility (72 h) of 84.6% for the solid residue from pretreatment at 110° C. for 60 min in a glycerol solution containing the same amount of acid. A glucan digestibility (72 h) of 94.8% was achieved on a sample that had been steam exploded following glycerol pretreatment. This process resulted in an improvement in glucan digestibility of about 10% compared to the pretreatment without steam explosion at the same pre-hydrolysis reaction temperature and time. All of the pretreatments with dilute acid only resulted in glucan digestibilities (72 h) less than 70%.

Compared to the laboratory scale pretreatment results, it appears that less severe pretreatment conditions (lower amounts of acid, lower temperatures, shorter pretreatment times, higher water contents, and higher solid loadings) can be used at the pilot plant scale to achieve similar enzymatic digestibility outcomes. This outcome is consistent with the results from other work done on the pilot plant scale. While not wishing to be bound to any particular theory, a few possible explanations for this outcome may relate to one or more of the following: improved heat transfer in larger scale reactors, better mixing, and the impact of larger fibre particle sizes on bulk properties of the fluid. Additionally, while not wishing to be bound to any particular theory, effective steam explosion is difficult to achieve at laboratory scales as a result of the relativity between fibre particle size and steam explosion equipment dimensions.

Figure 7:
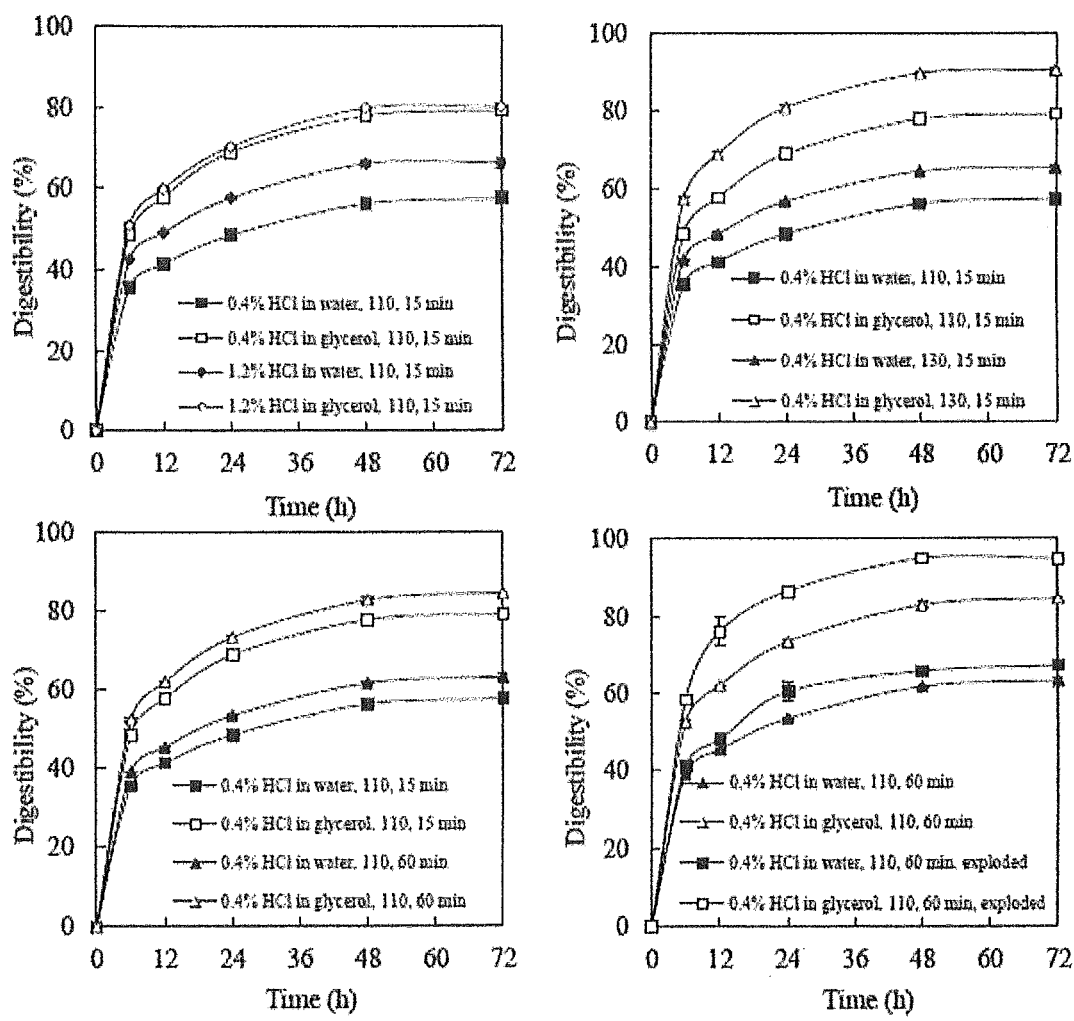
FIG. 7 shows graphs of the kinetics of enzymatic hydrolysis of pretreated sugarcane bagasse carried out at the pilot plant scale.

The kinetics of enzymatic hydrolysis of the solid residues from bagasse pretreated by glycerol/acid and water/acid solutions are shown in FIG. 7. The enzymatic hydrolysis rates were very rapid for the first 6 h. For most samples, after 48 h the increase in glucan digestibility was not significant.

The concentrations and yields of the key sugar degradation components 5-hydroxymethylfurfural (HMF) and furfural in the pretreatment hydrolysate are shown in Table 16. Much lower concentrations of HMF (glucose derivative) and furfural (xylose derivative) were produced with glycerol/HCl pretreatment solutions than with the water/HCl pretreatment solutions. The yields of HMF and furfural compared to the total initial sugarcane bagasse were also very low. The yield of 3-monochloropropane-1,2-diol (3-MCPD, a product from glycerol chlorination) was less than 0.37 g/kg hydrolysate or less than 0.61 g/kg initial glycerol under all conditions. This validated previous results that showed that the presence of water in the pretreatment solution reduced the production of glycerol chlorination products.

TABLE 16

Concentrations and yields of major components in pretreatment hydrolysate.

| Pretreatment conditions | Concentration (g/kg) | | | Yield on bagasse (g/kg) | | 3-MCPD yield (g/kg glycerol) |
|---|---|---|---|---|---|---|
| | HMF | Furfural | 3-MCPD | HMF | Furfural | |
| 0.4% HCl in water, 110° C., 15 min | 0.07 | 1.42 | N/A[1] | N/D[2] | N/D | N/A |
| 0.4% HCl in glycerol, 110° C., 15 min | 0.02 | 0.37 | 0.30 | 0.01 | 0.27 | 0.44 |
| 1.2% HCl in water, 110° C., 15 min | 0.16 | 3.40 | N/A | N/D | N/D | N/A |
| 1.2% HCl in glycerol, 110° C., 15 min | 0.01 | 0.61 | 0.31 | 0.01 | 0.46 | 0.46 |
| 0.4% HCl in water, 130° C., 15 min | 0.29 | 2.40 | N/A | N/D | N/D | N/A |
| 0.4% HCl in glycerol, 130° C., 15 min | 0.03 | 1.58 | 0.37 | 0.03 | 1.34 | 0.61 |
| 0.4% HCl in water, 110° C., 60 min | 0.13 | 2.99 | N/A | N/D | N/D | N/A |
| 0.4% HCl in glycerol, 110° C., 60 min | 0.02 | 0.88 | 0.31 | 0.01 | 0.79 | 0.55 |

[1]N/A: not applicable.
[2]N/D: not determined because total liquid weight could not be estimated.

These results demonstrate the feasibility of the acid catalysed aqueous glycerol process. The enzymatic digestibilities of the solid residues from the process are significantly higher than the digestibilities of dilute acid pretreated residues under the same conditions. Significantly lower concentrations of fermentation inhibitory products (5-HMF and furfural) were produced at the pilot plant scale from the glycerol based process than the dilute acid pretreatment process under the same conditions.

Similar enzymatic digestibility outcomes were achieved in the pilot plant scale experiments compared to those achieved in the laboratory scale experiments despite less severe pretreatment conditions (e.g., lower amounts of acid, lower pretreatment temperatures, shorter pretreatment times, and higher water content) being used. Steam explosion of the solid residue following pre-hydrolysis resulted in a residue with higher digestibility.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method for producing a partially hydrolyzed lignocellulosic material, comprising pretreating a lignocellulosic material with a pretreatment solution comprising glycerol in an amount of 80% to 99% by weight of the pretreatment solution, an acid catalyst in an amount of 0.5% to 2% by weight of the pretreatment solution, and water in an amount of 5% to 20% by weight of the pretreatment solution, wherein the pretreating step is carried out at a temperature from about 80° C. to about 150° C., thereby producing a pretreated partially hydrolyzed lignocellulosic material, wherein less than 20% of the cellulose present in the lignocellulosic material is converted into glucose.

2. The method of claim 1, wherein the pretreating step is carried out for a period of time from about 1 minute to about 120 minutes.

3. The method of claim 1, wherein the pretreating step is carried out at a biomass loading from about 1% to about 20% by weight of the pretreatment solution.

4. The method of claim 1, wherein the partially hydrolyzed lignocellulosic material has a total recovered lignin content of at least 40% of the total lignin in the lignocellulosic material prior to the pretreating step.

5. The method of claim 1, wherein the pretreating step decreases the amount of hemicellulose in the lignocellulosic material by at least 40%.

6. The method of claim 1, wherein the pretreating step reduces the production of 5-hydroxymethylfurfural, furfural, and/or acetic acid.

7. The method of claim 1, wherein the preteated lignocellulosic material is separated from the pretreatment solution.

8. The method of claim 7, wherein the pretreatment solution is collected for reuse in pretreating additional lignocellulosic material.

9. The method of claim 1, further comprising washing the pretreated lignocellulosic material with a basic solution.

10. The method of claim 9, wherein the basic solution has a pH of about 11 or greater.

11. The method of claim 1, further comprising enzymatically hydrolyzing the pretreated lignocellulosic material to produce a fermentable sugar.

12. The method of claim 11, wherein enzymatic digestibility of the pretreated lignocellulosic material is increased by at least two times compared to untreated lignocellulosic material.

13. The method of claim 11, wherein the enzymatic hydrolysis step is carried out with microbially produced enzymes, plant produced enzymes, or any combination thereof.

14. The method of claim 11, wherein the enzymatic hydrolysis step is carried out with an enzyme selected from the group consisting of cellulases, ligninases, hemicellulases, xylanases, lipases, pectinases, amylases, proteinases, and any combination thereof.

15. The method of claim 11, wherein the fermentable sugar is selected from the group consisting of glucose, xylose, arabinose, galactose, mannose, rhamnose, sucrose, fructose, and any combination thereof.

16. The method of claim 1, wherein prior to the pretreating step the lignocellulosic material is treated with an acid solution at a temperature from about 80° C. to about 200° C., wherein the acid is present in an amount of about 0.1% to about 5% by weight of the acid solution.

* * * * *

UNITED STATES PATENT AND TRADEMARK OFFICE
CERTIFICATE OF CORRECTION

PATENT NO. : 9,447,539 B2
APPLICATION NO. : 14/100340
DATED : September 20, 2016
INVENTOR(S) : Zhang et al.

Page 1 of 1

It is certified that error appears in the above-identified patent and that said Letters Patent is hereby corrected as shown below:

In the Specification

Column 21, Line 63: Please correct "32%" to read -- 3.2% --

Signed and Sealed this
Twenty-fifth Day of April, 2017

Michelle K. Lee
*Director of the United States Patent and Trademark Office*